United States Patent
Ikemoto et al.

(10) Patent No.: US 6,982,344 B2
(45) Date of Patent: Jan. 3, 2006

(54) PROCESS FOR PREPARATION OF OPTICALLY ACTIVE SULFONAMIDES AND INTERMEDIATES FOR THEIR SYNTHESIS

(75) Inventors: Tomomi Ikemoto, Takarazuka (JP); Atsuko Nishiguchi, Itami (JP); Kiminori Tomimatsu, Minoo (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 10/399,165

(22) PCT Filed: Oct. 17, 2001

(86) PCT No.: PCT/JP01/09120

§ 371 (c)(1),
(2), (4) Date: Apr. 11, 2003

(87) PCT Pub. No.: WO02/32859

PCT Pub. Date: Apr. 25, 2002

(65) Prior Publication Data

US 2004/0049041 A1 Mar. 11, 2004

(30) Foreign Application Priority Data

Oct. 18, 2000 (JP) ........................................ 2000-323309

(51) Int. Cl.
  *C07C 311/51* (2006.01)
  *C07C 311/14* (2006.01)
  *C07C 311/28* (2006.01)
  *C07C 303/40* (2006.01)
  *C07B 57/00* (2006.01)

(52) U.S. Cl. ........................................ 560/12; 564/80
(58) Field of Classification Search .................. 560/12; 560/564/80
See application file for complete search history.

(56) References Cited

FOREIGN PATENT DOCUMENTS

| EP | 1063228 A1 | 12/2000 |
|----|------------|---------|
| JP | 07-026194  | 1/1995  |
| JP | 11-147873  | 6/1999  |
| WO | WO 95/09151 | 4/1995 |

OTHER PUBLICATIONS

Encyclopedia of Separation Technology, a Kirk–Othmer Encyclopedia (vols. 1 & 2), Douglas M. Ruthven, ed., John Willey & Sons, New York, 1997, table of contents and pp. 320–355 of volumn 1.*
Kagaku Souetsu No. 4; pp. 242 (May 1974); Japanese language document and English Translation.
Kagaku Sousetsu No. 4 p. 242 (May 5, 1974).

* cited by examiner

*Primary Examiner*—Brian J. Davis
(74) *Attorney, Agent, or Firm*—Elaine M. Ramesh; Mark Chao

(57) ABSTRACT

A method including resolution of a diastereomeric mixture represented by the formula

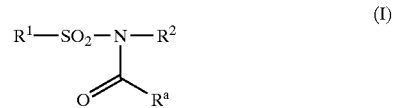

wherein $R^1$ and $R^2$ are the same or different and each is an optionally substituted hydrocarbon group or an optionally substituted heterocyclic group, only one of $R^1$ and $R^2$ contains one asymmetric carbon, and $R^a$ is an optically active and optionally substituted hydrocarbon group or an optically active and optionally substituted heterocyclic group, or a salt thereof, to produce the diastereomer having a steric configuration of the asymmetric carbon for $R^1$ or $R^2$ of an R configuration or an S configuration, or a salt thereof.

30 Claims, No Drawings

PROCESS FOR PREPARATION OF OPTICALLY ACTIVE SULFONAMIDES AND INTERMEDIATES FOR THEIR SYNTHESIS

This application is a 371 of PCT/JP01/09120 filed Oct. 17, 2001.

TECHNICAL FIELD

The present invention relates to a production method of pharmaceutical products, agrochemicals, foods, cosmetics and chemical products, and synthetic intermediates therefor.

BACKGROUND ART

There have been generally known three kinds of methods for obtaining an ontically active compound by chemical synthesis: optical resolution methods, induction methods and asymmetric synthesis methods.

However, there are problems in that 1) induction methods do not allow much choice in the starting substance, 2) asymmetric synthesis methods allow only a limited number of reactions to afford the objective substance at a high optical purity, and 3) from among the optical resolution methods, a method for resolution by high performance liquid chromatography (HPLC) using a chiral column is not an economical synthetic method suitable for mass synthesis.

Accordingly, a production method of an optically active compound, which is convenient and suitable for mass synthesis, is desired.

The present inventors have conducted various studies and, as a result, found a method for economically and conveniently producing an optically active form having a sulfonamide group, which comprises reaction of a racemate of sulfonamide having an asymmetric carbon with an optically active carboxylic acid to derive a diastereomeric form of acyl sulfonamide, optical resolution thereof to give an intermediate, and hydrolysis of the intermediate, which resulted in the completion of the present invention.

DISCLOSURE OF THE INVENTION

Accordingly, the present invention relates to

[1] a method comprising resolution of a diastereomeric mixture represented by the formula

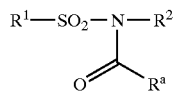

(I)

wherein
R¹ and R² are the same or different and each is an optionally substituted hydrocarbon group or an optionally substituted heterocyclic group, and only one of R¹ and R² contains one asymmetric carbon, and
Rᵃ is an optically active and optionally substituted hydrocarbon group or an optically active and optionally substituted heterocyclic group,
or a salt thereof, to produce a diastereomer having a steric configuration of the asymmetric carbon for R¹ or R² of an R configuration or an S configuration, or a salt thereof;
[2] the method of the above-mentioned [1], wherein Rᵃ is an optically active and optionally substituted hydrocarbon group containing an asymmetric carbon or an optically active and optionally substituted heterocyclic group containing an asymmetric carbon;
[3] the method of the above-mentioned [1], wherein the resolution is free of hydrolase;

[4] a production method of a diastereomeric mixture represented by the formula

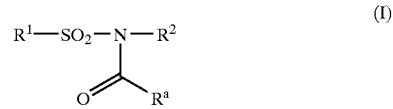

(I)

wherein R¹ and R² are the same or different and each is an optionally substituted hydrocarbon group or an optionally substituted heterocyclic group, and only one of R¹ and R² contains one asymmetric carbon, and Rᵃ is an optically active and optionally substituted hydrocarbon group or an optically active and optionally substituted heterocyclic group, or a salt thereof, which comprises reacting a racemate represented by the formula

$R^1$—$SO_2$—NH—$R^2$ (II)

wherein each symbol is as defined above, or a salt thereof with an optically active compound represented by the formula

$R^a$—COOH (III)

wherein Rᵃ is as defined above, or a salt thereof or a reactive derivative thereof;
[5] a production method of an optically active form represented by the formula

$R^{1a}$—$SO_2$—NH—$R^{2a}$ (V)

wherein $R^{1a}$ and $R^{2a}$ are the same or different and each is an optionally substituted hydrocarbon group or an optionally substituted heterocyclic group, only one of $R^{1a}$ and $R^{2a}$ contains one asymmetric carbon, and the steric configuration of the asymmetric carbon is an R configuration or an S configuration, or a salt thereof, which comprises deacylation of the diastereomer obtained in the above-mentioned [1] or a salt thereof;
[6] a production method of an optically active form represented by the formula

$R^{1a}$—$SO_2$—NH—$R^{2a}$ (V)

wherein $R^{1a}$ and $R^{2a}$ are the same or different and each is an optionally substituted hydrocarbon group or an optionally substituted heterocyclic group, only one of $R^{1a}$ and $R^{2a}$ contains one asymmetric-carbon, and a steric configuration of the asymmetric carbon is an R configuration or an S configuration, or a salt thereof, which comprises reacting a racemate represented by the formula

$R^1$—$SO_2$—NH—$R^2$ (II)

wherein R¹ and R² are the same or different and each is an optionally substituted hydrocarbon group or an optionally substituted heterocyclic group and only one of R¹ and R² contains one asymmetric carbon, or a salt thereof with an optically active compound represented by the formula

$R^a$—COOH (III)

wherein Rᵃ is an optically active and optionally substituted hydrocarbon group or an optically active and optionally substituted heterocyclic group, a salt thereof or a reactive derivative thereof to give a diastereomeric mixture represented by the formula

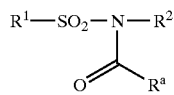
(I)

wherein each symbol is as defined above, or a salt thereof, resolving the diastereomeric mixture or a salt thereof to give the diastereomer wherein the asymmetric carbon for $R^1$ or $R^2$ has a steric configuration of an R configuration or an S configuration or a salt thereof, then deacylating said diastereomer;

[7] the method of any of the above-mentioned [1] to [6], wherein the group represented by the formula

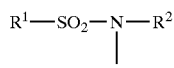

is a group represented by the formula

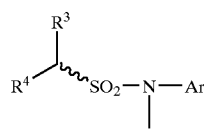
(A)

wherein $R^3$ and $R^4$ are the same or different and each is an optionally substituted hydrocarbon group or an optionally substituted heterocyclic group, $R^3$ and $R^4$ may form an optionally substituted cyclic group together with the adjacent carbon atom, Ar is an optionally substituted hydrocarbon group or an optionally substituted heterocyclic group, and the symbol ⌇ indicates a racemate, and the diastereomer comprises a group represented by the formula (A′)

wherein * shows the position of the asymmetric carbon and other symbols are as defined above, which has a steric configuration of the asymmetric carbon of an R configuration or an S configuration;

[8] the method of any of the above-mentioned [1] to [6], wherein the group represented by the formula

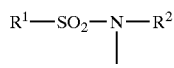

is a group represented by the formula

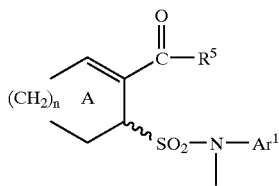
(B)

wherein $R^5$ is an optionally substituted hydrocarbon group, an optionally substituted heterocyclic group, the formula —$OR^6$ ($R^6$ is a hydrogen atom or an optionally substituted aliphatic hydrocarbon group) or the formula —$NR^7R^8$ ($R^7$ and $R^8$ are the same or different and each is a hydrogen atom or an optionally substituted aliphatic hydrocarbon group), $Ar^1$ is an optionally substituted aromatic hydrocarbon group, ring A may be further substituted, n is an integer of 1–4 and the symbol ⌇ indicates a racemate, and the diastereomer comprises a group represented by the formula

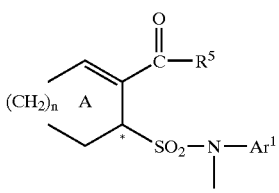
(B′)

wherein * shows the position of the asymmetric carbon and other symbols are as defined above, which has a steric configuration of the asymmetric carbon of an R configuration or an S configuration;

[9] the method of any of the above-mentioned [1] to [6], wherein the group represented by the formula

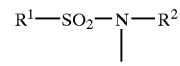

is a group represented by the formula

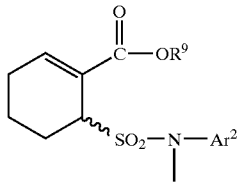
(C)

wherein $R^9$ is a $C_{1-6}$ alkyl group, $Ar^2$ is a $C_{6-14}$ aryl group optionally having a halogen atom, and the symbol ⌇ indicates a racemate, and the diastereomer comprises a group represented by the formula

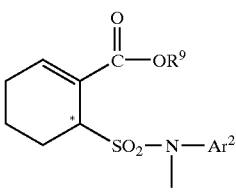

(C')

wherein * shows the position of the asymmetric carbon and other symbols are as defined above, which has a steric configuration of the asymmetric carbon of an R configuration or an S configuration;

[10] the method of the above-mentioned [4] or [6], wherein the compound represented by the formula

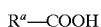

(III)

wherein $R^a$ is an optically active and optionally substituted hydrocarbon group or an optically active and optionally substituted heterocyclic group, is a compound containing an asymmetric carbon at the α-position of the carboxyl group;

[11] the method of the above-mentioned [10], wherein the compound represented by the formula

(III)

wherein $R^a$ is an optically active and optionally substituted hydrocarbon group or an optically active and optionally substituted heterocyclic group is (1) an optically active compound represented by the formula

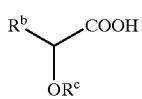

(IIIa)

wherein $R^b$ is a $C_{6-14}$ aryl group and $R^c$ is a $C_{1-6}$ alkanoyl group or a $C_{1-4}$ alkyl group, or a salt thereof, or (2) an optically active compound represented by the formula

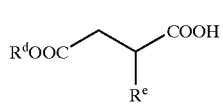

(IIIb)

wherein $R^d$ and $R^e$ are the same or different and each is a $C_{1-4}$ alkyl group, or a salt thereof;

[12] a compound represented by the formula

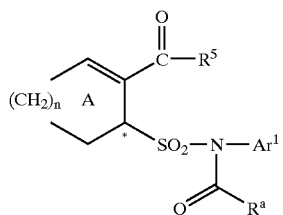

(IVb)

wherein
$R^a$ is an optically active and optionally substituted hydrocarbon group or an optically active and optionally substituted heterocyclic group,
$R^5$ is an optionally substituted hydrocarbon group, an optionally substituted heterocyclic group, a group represented by the formula —$OR^6$ ($R^6$ is a hydrogen atom or an optionally substituted aliphatic hydrocarbon group) or a group represented by the formula —$NR^7R^8$ ($R^7$ and $R^8$ are the same or different and each is a hydrogen atom or an optionally-substituted aliphatic hydrocarbon group),
$Ar^1$ is an optionally substituted aromatic hydrocarbon group,
ring A may be further substituted,
n is an integer of 1–4, and
* shows the position of an asymmetric carbon, or a salt thereof;

[13] the compound of the above-mentioned [12], wherein $R^aCO$— is a group represented by the formula

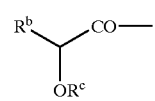

(IIIaa)

wherein $R^b$ is a $C_{6-14}$ aryl group and $R^c$ is a $C_{1-6}$ alkanoyl group or a $C_{1-4}$ alkyl group;

[14] the compound of the above-mentioned [12], wherein $R^aCO$— is a group represented by the formula

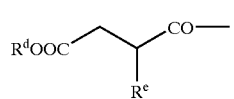

(IIIbb)

wherein $R^d$ and $R^e$ are the same or different and each is a $C_{1-4}$ alkyl group;

[15] (6R)-6-({[(2S)-2-(acetyloxy)-2-phenylethanoyl]-2-chloro-4-fluoroanilino}sulfonyl)-1-cyclohexene-1-carboxylic acid ethyl ester;

[16] (6R)-6-({2-chloro-4-fluoro[(2R)-4-methoxy-2-methyl-4-oxobutanoyl]anilino}sulfonyl)-1-cyclohexene-1-carboxylic acid ethyl ester;

[17] (6S)-6-({[(2R)-2-(acetyloxy)-2-phenylethanoyl]-2-chloro-4-fluoroanilino}sulfonyl)-1-cyclohexene-1-carboxylic acid ethyl ester; and

[18] (6S)-6-({2-chloro-4-fluoro[(2S)-4-methoxy-2-methyl-4-oxobutanoyl]anilino}sulfonyl)-1-cyclohexene-1-carboxylic acid ethyl ester.

In the present specification, as the "hydrocarbon group" of the "optionally substituted hydrocarbon group", for example, an alkyl group, a cycloalkyl group, a cycloalkylalkyl group, an alkenyl group, a cycloalkenyl group, an alkynyl group, an aryl group, an aralkyl group and the like are preferable.

As the alkyl group, for example, a linear or branched alkyl group having 1 to 20 carbon atoms (e.g., a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, a decyl group, a dodecyl group, etc.), and the like are preferable, and particularly, for example, a lower alkyl group having 1 to 6 carbon atoms (e.g., a methyl group, an ethyl group, an n-propyl group, an isopropyl group, an n-butyl group, an isobutyl group, a sec-butyl group, a tert-butyl group, etc.), and the like are preferable.

As the cycloalkyl group, for example, a cycloalkyl group having 3 to 10 carbon atoms (e.g., a cyclopropyl group, a cyclobutyl group, a cyclopentyl group, a cyclohexyl group, a cycloheptyl group, a cyclooctyl group, etc.), and the like are preferable, and particularly, for example, a cycloalkyl group having 3 to 6 carbon atoms (e.g., a cyclopropyl group, a cyclobutyl group, a cyclopentyl group, a cyclohexyl group, etc.), and the like are preferable.

As the cycloalkylalkyl group, for example, a cycloalkylalkyl group having 4 to 12 carbon atoms (e.g., a cyclopropylmethyl group, a cyclopentylmethyl group, a cyclohexylmethyl group, a cycloheptylmethyl group, etc.), and the like are preferable, and particularly, for example, a cycloalkylalkyl group having 4 to 8 (particularly 4 to 7) carbon atoms (e.g., a cyclopropylmethyl group, a cyclopentylmethyl group, a cyclohexylmethyl group, etc.), and the like are preferable.

As the alkenyl group, for example, a lower alkenyl group having 3 to 6 carbon atoms (e.g., a propenyl group, a butenyl group, a pentenyl group, etc.) are preferable, and particularly, for example, a lower alkenyl group having 3 or 4 carbon atoms (e.g., a propenyl group, a butenyl group, etc.), and the like are preferable.

As the cycloalkenyl group, for example, a cycloalkenyl group having 5 to 8 carbon atoms (e.g., a cyclobutenyl, a cyclopentenyl group, a cyclohexenyl group, a cycloheptenyl and the like) and the like are preferable. Particularly, for example, a cycloalkenyl group having 5 to 7 carbon atoms, such as a cyclopentenyl group, a cyclohexenyl group and the like, are preferable.

As the alkynyl group, for example, a lower alkynyl group having 3 to 6 carbon atoms (e.g., a propynyl group, a butynyl group, a pentynyl group, etc.) are preferable, and particularly, for example, a lower alkynyl group having 3 or 4 carbon atoms (e.g., a propynyl group, a butynyl group, etc.), and the like are preferable.

As the aryl group, for example, an aryl group having 6 to 14 carbon atoms (e.g., a phenyl group, a naphthyl group, a biphenyl group, an anthryl group, an indenyl group and the like) and the like are preferable. Particularly, for example, an aryl group having 6 to 10 carbon atoms (e.g., a phenyl group, a naphthyl group and the like) and the like are preferable, and phenyl group and the like are particularly preferable.

As the aralkyl group, for example, an arylalkyl group having 7 to 16 carbon atoms (e.g., a $C_{6-10}$ aryl-$C_{1-6}$ alkyl group such as a benzyl group, a phenylethyl group and the like, and the like), and the like are preferable. Particularly, a benzyl group and the like are preferable.

As the "substituents" of the "hydrocarbon group" of the above-mentioned "optionally substituted aliphatic hydrocarbon group", for example, a heterocyclic group, an oxo group, a hydroxy group, a $C_{1-6}$ alkoxy group, a $C_{3-10}$ (particularly $C_{3-6}$) cycloalkyloxy group, a $C_{6-10}$ aryloxy group, a $C_{7-19}$ (particularly $C_{7-12}$) aralkyloxy group, a heterocyclic oxy group, a $C_{1-6}$ alkylthio group (sulfur atom may be oxidized), a $C_{3-10}$ (particularly $C_{3-6}$) cycloalkylthio group (sulfur atom may be oxidized), a $C_{6-10}$ arylthio group (sulfur atom may be oxidized), a $C_{7-19}$ (particularly $C_{7-12}$) aralkylthio group (sulfur atom may be oxidized), a heterocyclic thio group, a heterocyclic sulfinyl group, a heterocyclic sulfonyl group, a nitro group, a halogen atom, a cyano group, a carboxyl group, a $C_{1-10}$ (particularly $C_{1-6}$) alkoxy-carbonyl group, a $C_{3-6}$ cycloalkyloxy-carbonyl group, a $C_{6-10}$ aryloxy-carbonyl group, a $C_{7-19}$ (particularly $C_{7-12}$) aralkyloxy-carbonyl group, a heterocyclic oxycarbonyl group, a $C_{6-10}$ aryl-carbonyl group, $C_{1-6}$ alkanoyl group, $C_{3-5}$ alkenoyl group, a $C_{6-10}$ aryl-carbonyloxy group, a $C_{2-6}$ alkanoyloxy group, a $C_{3-5}$ alkenoyloxy group, an optionally substituted carbamoyl group, an optionally substituted thiocarbamoyl group, an optionally substituted carbamoyloxy group, a $C_{1-6}$ alkanoylamino group, a $C_{6-10}$ aryl-carbonylamino group, a $C_{1-10}$ (particularly $C_{1-6}$) alkoxy-carboxamide group, a $C_{6-10}$ aryloxy-carboxamide group, a $C_{7-19}$ (particularly $C_{7-12}$) aralkyloxy-carboxamide group, a $C_{1-10}$ (particularly $C_{1-6}$) alkoxy-carbonyloxy group, a $C_{6-10}$ aryloxy-carbonyloxy group, a $C_{7-19}$ (particularly $C_{7-12}$) aralkyloxy-carbonyloxy group, a $C_{3-10}$ (particularly $C_{3-6}$) cycloalkyloxy-carbonyloxy group, an optionally substituted ureido group, an optionally substituted $C_{6-10}$ aryl group, etc. are used.

These substituents are substituted at substitutable positions in the above-mentioned "aliphatic hydrocarbon group", wherein the substituents are not limited to a single substituent but may be the same or different plural (2 to 4) substituents.

Among the substituents of the above-mentioned "hydrocarbon group", as the "$C_{1-6}$ alkoxy group", for example, a methoxy group, an ethoxy group, an n-propoxy group, an isopropoxy group, an n-butoxy group, a tert-butoxy group, an n-pentyloxy group, an n-hexyloxy group, etc. are used, as the "$C_{3-10}$ cycloalkyloxy group", for example, a cyclopropyloxy group, a cyclohexyloxy group, etc. are used, as the "$C_{6-10}$ aryloxy group", for example, a phenoxy group, a naphthyloxy group, etc. are used, as the "$C_{7-19}$ aralkyloxy group", for example, a benzyloxy group, a 1-phenylethyloxy group, a 2-phenylethyloxy group, a benzhydryloxy group, a 1-naphthylmethyloxy group, etc. are used, as the "$C_{1-6}$ alkylthio group (sulfur atom may be oxidized)", for example, a methylthio group, an ethylthio group, an n-propylthio group, an n-butylthio group, a methylsulfinyl group, a methylsulfonyl group, etc. are used, as the "$C_{3-10}$ cycloalkylthio group (the sulfur atom may be oxidized)", for example, a cyclopropylthio group, a cyclohexylthio group, a cyclopentylsulfinyl group, a cyclohexylsulfonyl group, etc. are used, as the "$C_{6-10}$ arylthio group (sulfur atom may be oxidized)", for example, a phenylthio group, a naphthylthio group, a phenylsulfinyl group, a phenylsulfonyl group, etc. are used, as the "$C_{7-19}$ aralkylthio group (sulfur atom may be oxidized)", for example, a benzylthio group, a phenylethylthio group, a benzhydrylthio group, a benzylsulfinyl group, a benzylsulfonyl group, etc. are used, as the "halogen atom", for example, a fluorine atom, a chlorine atom, a bromine atom or an iodine atom are used, as the "$C_{1-10}$ alkoxy-carbonyl group", for example, a methoxycarbonyl group, an ethoxycarbonyl group, an n-propoxycarbonyl group, an isopropoxycarbonyl group, an n-butoxycarbonyl group, an isobutoxycarbonyl group, a tert-butoxycarbonyl group, etc. are used, as the "$C_{3-6}$ cycloalkyloxy-carbonyl group", for example, a cyclopropyloxycarbonyl group, a cyclopentyloxycarbonyl group, a cyclohexyloxycarbonyl group, a norbornyloxycarbonyl group, etc. are used, as the "$C_{6-10}$ aryloxy-carbonyl group", for example, a phenoxycarbonyl group, a naphthyloxycarbonyl group, etc. are used, as the "$C_{7-19}$ aralkyloxy-carbonyl group", for example, a benzyloxycarbonyl group, a benzhydryloxycarbonyl group, a 2-phenethyloxycarbonyl group, etc. are used, as the "$C_{6-10}$ aryl-carbonyl group", for example, a benzoyl group, a naphthoyl group, a phenylacetyl group, etc. are used, as the "$C_{1-6}$ alkanoyl group", for example, a formyl group, an acetyl group, a propionyl group, a butyryl group, a valeryl group, a pivaloyl group, etc. are used, as the "$C_{3-5}$ alkenoyl group", for example, an acryloyl group, a crotonoyl group, etc. are used, as the "$C_{6-10}$ aryl-carbonyloxy group", for example, a benzoyloxy group, a naphthoyloxy group, a phenylacetoxy group, etc. are used, as the "$C_{2-6}$ alkanoyloxy group", for example, an acetoxy group, a propionyloxy group, a butyryloxy group, a valeryloxy group, a pivaloyloxy group, etc. are used, and as the "$C_{3-5}$ alkenoyloxy group", for example, an acryloyloxy group, a crotonoyloxy group, etc. are used.

As the "optionally substituted carbamoyl group", for example, a carbamoyl group or a cyclic aminocarbonyl group, which may be substituted by 1 or 2 groups selected from a $C_{1-4}$ alkyl (e.g., a methyl, an ethyl, etc.), a phenyl, a $C_{1-7}$ acyl (e.g., an acetyl, a propionyl, a benzoyl, etc.), a $C_{1-4}$ alkoxy-phenyl (e.g., a methoxyphenyl, etc.), etc. are used, and specifically, for example, a carbamoyl group, an N-methylcarbamoyl group, an N-ethylcarbamoyl group, an N,N-dimethylcarbamoyl group, an N,N-diethylcarbamoyl group, an N-phenylcarbamoyl group, an N-acetylcarbamoyl group, an N-benzoylcarbamoyl group, an N-(p-methoxyphenyl)carbamoyl group, a 1-pyrrolidinylcarbonyl group, a piperidinocarbonyl group, a 1-piperazinylcarbonyl group, a morpholinocarbonyl group, etc. are used. As the "optionally substituted thiocarbamoyl group", for example, a thiocarbamoyl group which may be substituted by 1 or 2 groups selected from a $C_{1-4}$ alkyl (e.g., a methyl, an ethyl, etc.), a phenyl, etc. are used, and specifically, for example, a thiocarbamoyl group, an N-methylthiocarbamoyl group, an N-phenylthiocarbamoyl group, etc. are used. As the "optionally substituted carbamoyloxy group", for example, a carbamoyloxy group which may be substituted by 1 or 2 groups selected from a $C_{1-4}$ alkyl (e.g., a methyl, an ethyl, etc.), a phenyl, etc. are used, and specifically, for example, a carbamoyloxy group, an N-methylcarbamoyloxy group, an N,N-dimethylcarbamoyloxy group, an N-ethylcarbamoyloxy group, an N-phenylcarbamoyloxy group, etc. are used.

As the "$C_{1-6}$ alkanoyiamino group", for example, an acetamide group, a propionamide group, a butyroamide group, a valeroamide group, a pivaloamide group, etc. are used, as the "$C_{6-10}$ aryl-carbonylamino group", for example, a benzamide group, a naphthoamide group, a phthalimide group, etc. are used, as the "$C_{1-10}$ alkoxy-carboxamide group", for example, a methoxycarboxamide ($CH_3OCONH$—) group, an ethoxycarboxamide group, a tert-butoxycarboxamide group, etc. are used, as the "$C_{6-10}$ aryloxy-carboxamide group", for example, a phenoxycarboxamide ($C_6H_5OCONH$—) group, etc. are used, as the "$C_{7-10}$ aralkyloxy-carboxamide group", for example, a benzyloxycarboxamide ($C_6H_5CH_2OCONH$—) group, a benzhydryloxycarboxamide group, etc. are used, as the "$C_{1-10}$ alkoxy-carbonyloxy group", for example, a methoxycarbonyloxy group, an ethoxycarbonyloxy group, an n-propoxycarbonyloxy group, an isopropoxycarbonyloxy group, an n-butoxycarbonyloxy group, a tert-butoxycarbonyloxy group, an n-pentyloxycarbonyloxy group, an n-hexyloxycarbonyloxy group, etc. are used, as the "$C_{6-10}$ aryloxy-carbonyloxy group", for example, a phenoxycarbonyloxy group, a naphthyloxycarbonyloxy group, etc. are used, as the "$C_{7-10}$ aralkyloxy-carbonyloxy group", for example, a benzyloxycarbonyloxy group, a 1-phenylethyloxycarbonyloxy group, a 2-phenylethyloxycarbonyloxy group, a benzhydryloxycarbonyloxy group, etc. are used, and as the "$C_{3-10}$ cycloalkyloxy-carbonyloxy group", for example, a cyclopropyloxycarbonyloxy group, a cyclohexyloxycarbonyloxy group, etc. are used.

As the "optionally substituted ureido group", for example, a ureido group optionally substituted by 1 to 3 (preferably 1 or 2) substituents selected from a $C_{1-4}$ alkyl group (e.g., a methyl group, an ethyl group, etc.), a phenyl group, etc. are used, and, for example, a ureido group, a 1-methylureido group, a 3-methylureido group, a 3,3-dimethylureido group, a 1,3-dimethylureido group, a 3-phenylureido group, etc. are used.

When a heterocyclic group, a heterocyclic oxy group, a heterocyclic thio group, a heterocyclic sulfinyl group, a heterocyclic sulfonyl group or a heterocyclic oxycarbonyl group is used as the "substituents" of the "hydrocarbon" of the "optionally substituted hydrocarbon group", the heterocyclic group represents a group formed by excluding one hydrogen atom that binds to the heterocycle, and it represents, for example, a 5-to 8-membered cyclic (preferably 5-or 6-membered cyclic) group containing 1 to a few, preferably 1 to 4 hetero atoms such as a nitrogen atom (optionally oxidized), an oxygen atom, a sulfur atom, etc., or its condensed cyclic group. As these heterocyclic groups, for example, a pyrrolyl group, a pyrazolyl group, an imidazolyl group, a 1,2,3-triazolyl group, a 1,2,4-triazolyl group, a tetrazolyl group, a furyl group, a thienyl group, an oxazolyl group, an isoxazolyl group, a 1,2,3-oxadiazolyl group, a 1,2,4-oxadiazolyl group, a 1,2,5-oxadiazolyl group, a 1,3,4-oxadiazolyl group, a thiazolyl group, an isothiazolyl group, a 1,2,3-thiadiazolyl group, a 1,2,4-thiadiazolyl group, a 1,2,5-thiadiazolyl group, a 1,3,4-thiadiazolyl group, a pyridyl group, a pyridazinyl group, a pyrimidinyl group, a pyrazinyl group, an indolyl group, a pyranyl group, a thiopyranyl group, a dioxinyl group, a dioxolyl group, a quinolyl group, a pyrido[2,3-d]pyrimidyl group, a 1,5-, 1,6-, 1,7-, 1,8-, 2,6-or 2,7-naphthyridyl group, a thieno[2,3-d] pyridyl group, a benzopyranyl group, a tetrahydrofuryl group, a tetrahydropyranyl group, a dioxolanyl group, a dioxanyl group, etc. are used.

These heterocyclic groups may be substituted at substitutable positions by 1 to 3 substituents selected from a $C_{1-4}$ alkyl (e.g., methyl, ethyl, etc.), a hydroxy, an oxo, a $C_{1-4}$ alkoxy (e.g., methoxy, ethoxy, etc.), and the like.

As the "$C_{6-10}$ aryl group" of the "$C_{6-10}$ aryl group optionally having substituents", for example, a phenyl group, a naphthyl group, etc. are used. The $C_{6-10}$ aryl group may be substituted at a substitutable position by a substituent selected from those exemplified as the "substituent" (except for an optionally substituted $C_{6-10}$ aryl group) of the "optionally substituted hydrocarbon group" described above. These substituents are substituted at substitutable positions of the $C_{6-10}$ aryl group, wherein such substituents are not limited to a single substituent, but the same or different, more than one (2 to 4) substituents may be used.

In the "optionally substituted hydrocarbon group", the substituent together with the aliphatic hydrocarbon group may form an optionally substituted condensed ring group, and as such condensed ring group, an indanyl group, a 1,2,3,4-tetrahydronaphthyl group, etc. are used. This condensed ring group may be substituted at substitutable positions by substituents selected from those exemplified as the "substituent" of the "aliphatic hydrocarbon optionally having substituents" described above. Such substituents are substituted at substitutable positions of the condensed ring group, wherein the substituents are not limited to a single substituent, but the same or different, more than one (2 to 4) substituents may be used.

When the hydrocarbon group is a cyclic hydrocarbon group such as a cycloalkyl group, a cycloalkylalkyl group, a cycloalkenyl group, an aryl group or an aralkyl group (particularly, a cycloalkenyl group) and the like, the substituent may have a group represented by the formula

wherein $R^5$ is an optionally substituted hydrocarbon group, an optionally substituted heterocyclic group, a group represented by the formula —$OR^6$ ($R^6$ is a hydrogen atom or an optionally substituted aliphatic hydrocarbon group) or a group represented by the formula —$NR^7R^8$ ($R^7$ and $R^8$ are the same or different and each is a hydrogen atom or an optionally substituted aliphatic hydrocarbon group).

In the present specification, the "heterocyclic group" in the "optionally substituted heterocyclic group" means, for example, a 5- to 8-membered ring (preferably 5- or 6-membered ring) group having 1 to several, preferably 1 to 4, hetero atoms, such as a nitrogen atom (optionally oxidized), an oxygen atom, a sulfur atom and the like, or its condensed ring group.

As these heterocyclic groups, for example, a pyrrolyl group, a pyrazolyl group, an imidazolyl group, a 1,2,3-triazolyl group, a 1,2,4-triazolyl group, a tetrazolyl group, a furyl group, a thienyl group, an oxazolyl group, an isoxazolyl group, a 1,2,3-oxadiazolyl group, a 1,2,4-oxadiazolyl group, a 1,2,5-oxadiazolyl group, a 1,3,4-oxadiazolyl group, a thiazolyl group, an isothiazolyl group, a 1,2,3-thiadiazolyl group, a 1,2,4-thiadiazolyl group, a 1,2,5-thiadiazolyl group, a 1,3,4-thiadiazolyl group, a pyridyl group, a pyridazinyl group, a pyrimidinyl group, a pyrazinyl group, an indolyl group, a pyranyl group, a thiopyranyl group, a dioxinyl group, a dioxolyl group, a quinolyl group, a pyrido[2,3-d]pyrimidinyl group, 1,5-, 1,6-, 1,7-, 1,8-, 2,6-or 2,7-naphthyridyl group, a thieno[2,3-d]pyridyl group, a benzopyranyl group, a tetrahydrofuryl group, a tetrahydropyranyl group, a dioxolanyl group, a dioxanyl group, etc. are used.

As the "substituent" of the "optionally substituted heterocyclic group", for example, those similar to the "substituent" of the aforementioned "optionally substituted hydrocarbon group" are used. Particularly, a $C_{1-4}$ alkyl group (e.g., a methyl group, an ethyl group and the like), a hydroxy group, an oxo group, a $C_{1-4}$ alkoxy group (e.g., a methoxy group, an ethoxy group and the like) and the like are preferable. These substituents are substituted at substitutable positions in the above-mentioned "heterocyclic group", wherein the substituents are not limited a single substituent but may be the same or different plural (2 to 4) substituents.

In the present specification, as the "aliphatic hydrocarbon group" of the "optionally substituted aliphatic hydrocarbon group", for example, an alkyl group, a cycloalkyl group, a cycloalkylalkyl group, an alkenyl group, an alkynyl group and the like are preferable.

As the alkyl group, for example, a linear or branched alkyl group having 1 to 20 carbon atoms (e.g., a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, a decyl group, a dodecyl group, etc.), and the like are preferable, and particularly, for example, a lower alkyl group having 1 to 6 carbon atoms (e.g., a methyl group, an ethyl group, an n-propyl group, an isopropyl group an n-butyl group, an isobutyl group, a sec-butyl group, a tert-butyl group, etc.), and the like are preferable.

As the cycloalkyl group, for example, a cycloalkyl group having 3 to 10 carbon atoms (e.g., a cyclopropyl group, a cyclobutyl group, a cyclopentyl group, a cyclohexyl group, a cycloheptyl group, a cyclooctyl group, etc.), and the like are preferable, and particularly, for example, a cycloalkyl group having 3 to 6 carbon atoms (e.g., a cyclopropyl group, a cyclobutyl group, a cyclopentyl group, a cyclohexyl group, etc.), and the like are preferable.

As the cycloalkylalkyl group, for example, a cycloalkylalkyl group having 4 to 12 carbon atoms (e.g., a cyclopropylmethyl group, a cyclopentylmethyl group, a cyclohexylmethyl group, a cycloheptylmethyl group, etc.), and the like are preferable, and particularly, for example, a cycloalkylalkyl group having 4 to 8 (particularly 4 to 7) carbon atoms (e.g., a cyclopropylmethyl group, a cyclopentylmethyl group, a cyclohexylmethyl group, etc.), and the like are preferable.

As the alkenyl group, for example, a lower alkenyl group having 3 to 6 carbon atoms (e.g., a propenyl group, a butenyl group, a pentenyl group, etc.) are preferable, and particularly, for example, a lower alkenyl group having 3 or 4 carbon atoms (e.g., a propenyl group, a butenyl group, etc.), and the like are preferable.

As the alkynyl group, for example, a lower alkynyl group having 3 to 6 carbon atoms (e.g., a propynyl group, a butynyl group, a pentynyl group, etc.) are preferable, and particularly, for example, a lower alkynyl group having 3 or 4 carbon atoms (e.g., a propynyl group, a butynyl group, etc.), and the like are preferable.

As the "substituent" of the "optionally substituted aliphatic hydrocarbon", for example, those similar to the "substituent" of the aforementioned "optionally substituted hydrocarbon group" are used. These substituents are substituted at substitutable positions in the above-mentioned "aliphatic hydrocarbon group", wherein the substituents are not limited a single substituent but may be the same or different plural (2 to 4) substituents.

In the present specification, as the "aromatic hydrocarbon group" of the "optionally substituted aromatic hydrocarbon group", an aromatic hydrocarbon group having 6 to 14 carbon atoms (e.g., a phenyl group, a naphthyl group, a biphenyl group, an anthryl group, an indenyl group and the like) and the like are preferable, and particularly for example, an aryl group having 6 to 10 carbon atoms (e.g., phenyl and naphthyl groups etc.) and the like are preferable and, of these, a phenyl group and the like are particularly preferable.

As the "substituent" of the "optionally substituted aromatic hydrocarbon group", for example, those similar to the "substituent" of the "optionally substituted hydrocarbon group" are used of these, a halogen atom (e.g., fluorine, chlorine, bromine, iodine and the like), a lower ($C_{1-4}$) alkyl group (e.g., a methyl group, an ethyl group, a propyl group, a butyl group and the like), a lower ($C_{1-4}$) alkoxy group (e.g., a methoxy group, an ethoxy group, a propoxy group, a butoxy group and the like), a lower ($C_{1-4}$) alkoxycarbonyl group (e.g., a methoxycarbonyl group, an ethoxycarbonyl group, a propoxycarbonyl group, a butoxycarbonyl group and the like), a carboxyl group, a nitro group, a cyano group, a hydroxyl group, an acylamino group (e.g., an alkanoylamino group having 1 to 4 carbon atoms such as an acetylamino group, a propionylamino group, a butyrylamino group and the like, and the like), a cycloalkyl group having 3 to 6 carbon atoms (e.g., a cyclopropyl group, a cyclopentyl group and the like), an aryl group having 6 to 10 carbon atoms (e.g., a phenyl group, a naphthyl group, an indenyl group and the like), a halogeno-lower ($C_{1-4}$) alkyl group (e.g., a trifluoromethyl group, a trifluoroethyl group and the like), a halogeno-lower ($C_{1-4}$) alkoxy group (e.g., a trifluoromethoxy group, a 1,1,2,2-tetrafluoroethoxy group, a 2,2,3,3,3-pentafluoropropoxy group and the like), a lower ($C_{1-4}$) alkylthio group (e.g., a methylthio group, an ethylthio group, a propylthio group and the like), a lower ($C_{1-4}$) alkylsulfonyl group (e.g., a methanesulfonyl group, an ethanesulfonyl group, a propanesulfonyl group and the like), a lower ($C_{1-4}$) alkanoyl group (e.g., a formyl group, an acetyl group, a propionyl group and the like), a 5-membered aromatic heterocyclic group (e.g., a 1,2,3-triazolyl group, a 1,2,4-triazolyl group, a tetrazolyl group, a thiazolyl group, an isothiazolyl group, an oxazolyl group, an isoxazolyl group, a thiadiazolyl group, a thienyl group, a furyl group and the like), a carbamoyl group, a lower ($C_{1-4}$) alkyl-carbamoyl group (e.g., a methylcarbamoyl group, a dimethylcarbamoyl group, a propionylcarbamoyl group and the like), a lower ($C_{1-4}$) alkoxy-carbonyl-lower ($C_{1-4}$) alkylcarbamoyl group (e.g., a butoxycarbonylmethylcarbamoyl group, an ethoxycarbonylmethylcarbamoyl group and the like), a 1,3-diacylguanidino-lower ($C_{1-4}$) alkyl group (e.g., 1,3-diacetylguanidinomethyl, 1,3-bis-(tert-butoxycarbonyl) guanidinomethyl and the like) and the like are preferable. Furthermore, a halogen atom (e.g., fluorine, chlorine, bromine, iodine atoms), a lower ($C_{1-4}$) alkyl group (e.g., a methyl group, an ethyl group, a propyl group, a butyl group and the like) and the like are preferable, and a fluorine atom, a chlorine atom and a methyl group are particularly preferable.

These substituents are substituted at substitutable positions of the "aromatic hydrocarbon group", and the number of the substituents is preferably 1 to 5, more preferably 1 to 3, most preferably 1 or 2. When two or more of such substituents are present, they may be the same or different.

$R^1$ and $R^2$ are the same or different and each is an optionally substituted hydrocarbon group or an optionally substituted heterocyclic group, and only one of $R^1$ and $R^2$ contains one asymmetric carbon.

Therefore, one of $R^1$ and $R^2$ is an "optionally substituted hydrocarbon group" or an "optionally substituted heterocyclic group", which is free of an asymmetric carbon. The other is an "optionally substituted hydrocarbon group" or "optionally substituted heterocyclic group" having one asymmetric carbon, from among the aforementioned "optionally substituted hydrocarbon group" and the "optionally substituted heterocyclic group".

$R^{1a}$ and $R^{2a}$ are the same or different and each is an optionally substituted hydrocarbon group or an optionally substituted heterocyclic group, and only one of $R^{1a}$ and $R^{2a}$ contains one asymmetric carbon.

Therefore, one of $R^{1a}$ and $R^{2a}$ is an "optionally substituted hydrocarbon group" or an "optionally substituted heterocyclic group", which is free of an asymmetric carbon. The other is an "optionally substituted hydrocarbon group" or "Optionally substituted heterocyclic group" having one asymmetric carbon.

The position of the asymmetric carbon is not particularly limited but the α-position of a sulfonamide group is preferable.

$R^a$ shows an optically active and optionally substituted hydrocarbon group or an optically active and optionally substituted heterocyclic group. Preferably, $R^a$ is an optically active and optionally substituted hydrocarbon group containing an asymmetric carbon or an optically active and optionally substituted heterocyclic group containing an asymmetric carbon.

Therefore, $R^a$ is an optically active "optionally substituted hydrocarbon group" or an optically active "optionally substituted heterocyclic group" from among the aforementioned "optionally substituted hydrocarbon group" and "optionally substituted heterocyclic group", preferably an optically active "optionally substituted hydrocarbon group" or an optically active "optionally substituted heterocyclic group" containing an asymmetric carbon.

As used herein, the "optically active and optionally substituted hydrocarbon group" means (1) a group without a substituent or having a substituent without optical activity, wherein the hydrocarbon moiety is optically active, or (2) a group having an optically active substituent, wherein the hydrocarbon moiety is free of optical activity, with preference given to (1).

In addition, the "optically active and optionally substituted heterocyclic group" means (3) a group without a substituent or having a substituent without optical activity, wherein the heterocyclic moiety is optically active, or (4) a group having an optically active substituent, wherein the heterocyclic moiety is free of optical activity, with preference given to (3).

When $R^a$ contains an asymmetric carbon, the position of the asymmetric carbon is not particularly limited but the α-position of a carbonyl group is preferable.

As the group represented by the formula

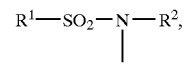

the groups represented by the formulas (A)–(C) and the like are preferable.

(1) A group represented by the formula

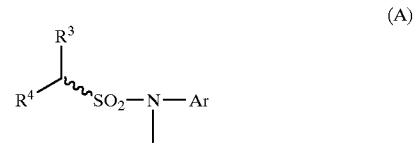

(A)

wherein $R^3$ and $R^4$ are the same or different and each is an optionally substituted hydrocarbon group or an optionally substituted heterocyclic group, $R^3$ and $R^4$ may form an optionally substituted cyclic group together with an adjacent carbon atom, Ar is an optionally substituted hydrocarbon group or an optionally substituted heterocyclic group, and the symbol ⁓
indicates a racemate.

(2) A group represented by the formula

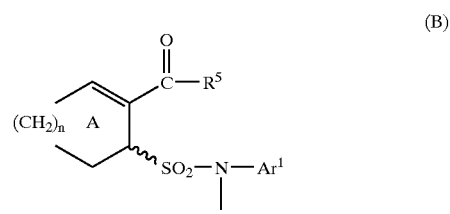

(B)

wherein $R^5$ is an optionally substituted hydrocarbon group, an optionally substituted heterocyclic group, a group represented by the formula —$OR^6$ ($R^6$ is a hydrogen atom or an optionally substituted aliphatic hydrocarbon group), a group represented by the formula —$NR^7R^8$ ($R^7$ and $R^8$ are the same or different and each is a hydrogen atom or an optionally substituted aliphatic hydrocarbon group,
$Ar^1$ is an optionally substituted aromatic hydrocarbon group, ring A may be further substituted, n is an integer of 1–4, and the symbol ⁓
indicates a racemate.

(3) A group represented by the formula

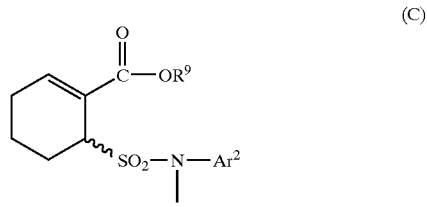

(C)

wherein $R^9$ is a $C_{1-6}$ alkyl group, $Ar^2$ is a $C_{6-14}$ aryl group optionally having a halogen atom, and the symbol ⌇ indicates a racemate.

The groups of the diastereomer corresponding to the groups represented by these (A)–(C) show groups represented by the following (A')–(C').

(1) A group represented by the formula

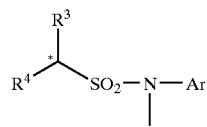
(A')

wherein * shows the position of an asymmetric carbon and other symbols are as defined above.

(2) A group represented by the formula (B')

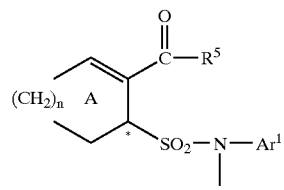
(B')

wherein * shows the position of an asymmetric carbon and other symbols are as defined above.

(3) A group represented by the formula (C')

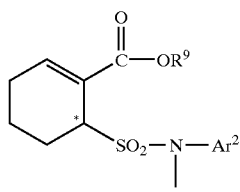
(C')

wherein * shows the position of an asymmetric carbon and other symbols are as defined above.

As $R^aCO-$, for example, (1) a group represented by the formula

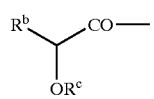
(IIIaa)

wherein $R^b$ is a $C_{6-14}$ aryl group and $R^c$ is a $C_{1-6}$ alkanoyl group, (2) a group represented by the formula

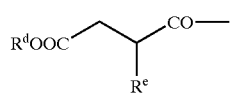
(IIIbb)

wherein $R^d$ and $R^e$ are the same or different and each is a $C_{1-4}$ alkyl group, (3) a group represented by the formula

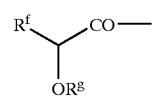
(IIIcc)

wherein $R^f$ is a $C_{6-14}$ aryl group and $R^g$ is a $C_{1-4}$ alkyl group, (4) a 5-or 6-membered oxygen-containing heterocyclic group (preferably an oxygen-containing non-aromatic heterocyclic group containing one or two oxygen atoms), such as a group represented by the formula

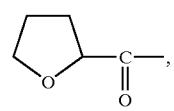
(III dd)

(5) a group represented by the formula

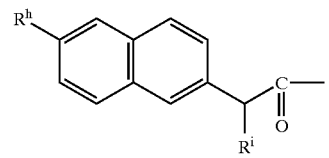
(III ee)

wherein $R^h$ and $R^i$ are the same or different and each is a $C_{1-6}$ alkyl group or a $C_{1-4}$ alkoxy group, (6) a group represented by the formula

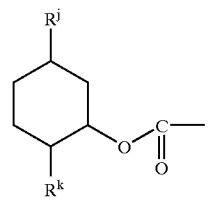
(III ff)

wherein $R^j$ and $R^k$ are the same or different and each is a $C_{1-6}$ alkyl group, and the like are used.

Of these, a group represented by the formula

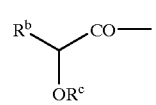
(IIIaa)

wherein each symbol is as defined above, a group represented by the formula

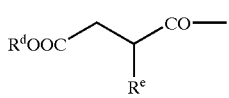
(IIIbb)

wherein each symbol is as defined above and the like are preferable.

That is, as a compound represented by the formula $$R^a\text{—COOH} \qquad \qquad (III)$$

wherein $R^a$ is as defined above,
(1) a compound represented by the formula

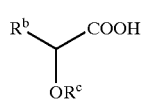 (IIIa)

wherein $R^b$ is a $C_{6-14}$ aryl group and $R^c$ is a $C_{1-6}$ alkanoyl group,
(2) a compound represented by the formula

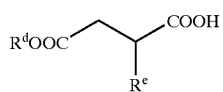 (IIIb)

wherein $R^d$ and $R^e$ are the same or different and each is a $C_{1-4}$ alkyl group and the like are preferable.

As a compound represented by the formula

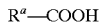 (III), an optically active compound containing an asymmetric carbon at the α-position of carboxyl group is preferable.

Explanation of Partial Structure (A)

As the "optionally substituted hydrocarbon group" and the "optionally substituted heterocyclic group" represented by $R^3$ and $R^4$, those as mentioned above are used.

As the "cyclic group" of the "optionally substituted cyclic group" formed by $R^3$ and $R^4$ together with the adjacent carbon atom, a 3- to 10-membered carbocyclic group, a 3- to 9-membered heterocyclic group containing, besides carbon atoms, 1 to 4 hetero atoms such as a nitrogen atom, an oxygen atom, a sulfur atom and the like, and the like are used.

As the 3- to 10-membered carbocyclic group, a $C_{3-7}$ cycloalkyl group (e.g., a cyclopropyl group, a cyclobutyl group, a cycloheptyl group, a cyclohexyl group), a $C_{3-7}$ cycloalkenyl group (e.g., a 2-cyclohexenyl group), a $C_{6-10}$ aryl group (e.g., a phenyl group, a naphthyl group) and the like are used, of which a $C_{3-7}$ cycloalkenyl group is preferable and a 2-cyclohexenyl group is particularly preferable.

As the 3- to 9-membered heterocyclic group containing, besides carbon atoms, 1 to 4 hetero atoms such as a nitrogen atom, an oxygen atom, a sulfur atom and the like, for example, a pyrrolyl group, a pyrazolyl group, an imidazolyl group, a 1,2,3-triazolyl group, a 1,2,4-triazolyl group, a tetrazolyl group, a furyl group, a thienyl group, an oxazolyl group, an isoxazolyl group, a 1,2,3-oxadiazolyl group, a 1,2,4-oxadiazolyl group, a 1,2,5-oxadiazolyl group, a 1,3,4-oxadiazolyl group, a thiazolyl group, an isothiazolyl group, a 1,2,3-thiadiazolyl group, a 1,2,4-thiadiazolyl group, a 1,2,5-thiadiazolyl group, a 1,3,4-thiadiazolyl group, a pyridyl group, a pyridazinyl group, a pyrimidinyl group, a pyrazinyl group, an indolyl group, a pyranyl group, a thiopyranyl group, a dioxinyl group, a dioxolyl group, a quinolyl group, a pyrido[2,3-d]pyrimidinyl group, 1,5-, 1,6-, 1,7-, 1,8-, 2,6- or 2,7-naphthyridyl group, a thieno[2,3-d]pyridyl group, a benzopyranyl group, a tetrahydrofuryl group, a tetrahydropyranyl group, a dioxolanyl group, a dioxanyl group- and the like are used, of which a 5- or 6-membered heterocyclic group is preferable.

As the substituent of the cyclic group formed by $R^3$ and $R^4$ together with the adjacent carbon atom, an optionally substituted hydrocarbon group (e.g., an optionally substituted aliphatic hydrocarbon group, an optionally substituted aromatic hydrocarbon group), an optionally substituted heterocyclic group, a group represented by —C(=O)—$R^5$ ($R^5$ is an optionally substituted hydrocarbon group or an optionally substituted heterocyclic group), a group represented by —C(=O)—$OR^6$ ($R^6$ is an optionally substituted aliphatic hydrocarbon group, an optionally substituted aromatic hydrocarbon group or an optionally substituted heterocyclic group), a group represented by —C(=O)—$NR^7R^8$ ($R^7$ and $R^8$ are the same or different and each is a hydrogen atom or an optionally substituted hydrocarbon group) and the like are used. While the number of the substituents is not particularly limited, it is, for example, 1 to 3.

As these "optionally substituted hydrocarbon group", "optionally substituted aliphatic hydrocarbon group", "optionally substituted aromatic hydrocarbon group" and "optionally substituted heterocyclic group", those similar to the aforementioned are used.

As the "optionally substituted hydrocarbon group" and the "optionally substituted heterocyclic group" represented by Ar, those similar to the aforementioned are used. Explanation of partial structure (B) As the "optionally substituted hydrocarbon group" and "optionally substituted heterocyclic group" represented by $R^5$, those similar to the aforementioned are used.

As the "optionally substituted aliphatic hydrocarbon group" represented by $R^6$, $R^7$ and $R^8$, those similar to the aforementioned are used.

As the $R^5$, a group represented by the formula —$OR^6$ ($R^6$ is as defined above) is preferable.

As the $R^6$, for example, an optionally substituted lower alkyl group having 1 to 6 carbon atoms (e.g., a methyl group, an ethyl group, an n-propyl group, an isopropyl group, an n-butyl group, an isobutyl group, a tert-butoxycarbonylmethyl group, a hydroxyethyl group and the like) and the like are preferably used. Of these, for example, a methyl group, an ethyl group, an n-propyl group, an isopropyl group, an n-butyl group, an isobutyl group and the like are preferably used. Among these, for example, a methyl group, an ethyl group, an n-propyl group and the like are preferable. Particularly, an ethyl group and the like are preferable.

As the "optionally substituted aromatic hydrocarbon group" represented by $Ar^1$, those similar to the aforementioned are used.

Typically, as $Ar^1$, for example, a phenyl group, a halogenophenyl group, a lower ($C_{1-4}$) alkyl-phenyl group, a lower ($C_{1-4}$) alkoxy-phenyl group, a lower ($C_{1-4}$) alkoxycarbonylphenyl group, a carboxylphenyl group, a nitrophenyl group, a. cyanophenyl group, a halogeno-lower ($C_{1-4}$) alkyl-phenyl group, a halogeno-lower ($C_{1-4}$) alkoxy-phenyl group, a lower ($C_{1-4}$) alkanoyl-phenyl group, a phenyl group substituted by a 5-membered aromatic heterocycle, a lower ($C_{1-4}$) alkoxy-carbonyl-lower ($C_{1-4}$) alkyl-carbamoylphenyl group, 1,3-diacylguanidino-lower ($C_{1-4}$) alkylphenyl group, a phenyl group substituted by halogen or lower ($C_{1-4}$) alkyl, a phenyl group substituted by a halogen and a lower ($C_{1-4}$) alkoxycarbonyl, a phenyl group substituted. by a halogen and a cyano, a phenyl group substituted by a halogen and a 5-membered aromatic heterocycle, a phenyl group substituted by a halogen and a lower ($C_{1-4}$) alkoxycarbonyl-lower ($C_{1-4}$) alkylcarbamoyl and the like are used.

As the halogenophenyl group, for example, a 2,3-difluorophenyl group, a 2,3-dichlorophenyl group, a 2,4-difluorophenyl group, a 2,4-dichlorophenyl group, a 2,5-difluorophenyl group, a 2,5-dichlorophenyl group, a 2,6-difluorophenyl group, a 2,6-dichlorophenyl group, a 3,4-difluorophenyl group, a 3,4-dichlorophenyl group, a 3,5- difluorophenyl group, a 3,5-dichlorophenyl group, a 2-fluorophenyl group, a 2-chlorophenyl group, a 3-fluorophenyl group, a 3-chlorophenyl group, a 4-fluorophenyl group, a 4-chlorophenyl group, a 2-fluoro-4-chlorophenyl group, a 2-chloro-4-fluorophenyl group, a 4-bromo-2-fluorophenyl group, a 2,3,4-trifluorophenyl group, a 2,4,5-trifluorophenyl group, a 2,4,6-trifluorophenyl and the like are used.

As the lower ($C_{1-4}$) alkyl-phenyl group, for example, a 2-ethylphenyl group, a 2,6-diisopropylphenyl group and the like are preferably used, and as the lower ($C_{1-4}$) alkoxy-phenyl group, for example, a 4-methoxyphenyl and the like are preferably used.

As the lower ($C_{1-4}$) alkoxy-carbonylphenyl group, for example, a 2-ethoxycarbonylphenyl group, a 2-methoxycarbonylphenyl group, a 4-methoxycarbonylphenyl group and the like are preferably used, and as the halogeno-lower ($C_{1-4}$) alkyl-phenyl group, for example, a 2-trifluoromethylphenyl group and the like are preferably used, and as the halogeno-lower ($C_{1-4}$) alkoxyphenyl group, for example, a 2-trifluoromethoxyphenyl group, a 4-(2,2,3,3,3-pentafluoropropoxy)phenyl group and the like are preferably used.

As the lower ($C_{1-4}$) alkanoyl-phenyl group, for example, a 2-acetylphenyl group and the like are preferably used, and as the phenyl group substituted by a 5-membered aromatic heterocycle, for example, a 4-(2H-1,2,3-triazol-2-yl)phenyl group, a 4-(2H-tetrazol-2-yl)phenyl group, a 4-(1H-tetrazol-1-yl)phenyl group, a 4-(1H-1,2,3-triazol-1-yl)phenyl group and the like are preferably used, and as the lower ($C_{1-4}$) alkoxycarbonyl-lower ($C_{1-4}$) alkyl-carbamoylphenyl group, for example, a 4-(N-ethoxycarbonylmethylcarbamoyl) phenyl group and the like are preferably used, and as the 1,3-diacylguanidino-lower ($C_{1-4}$) alkyl-phenyl group, for example, a 4-(1,3-bis-(tert-butoxycarbonyl) guanidinomethyl)phenyl group and the like are preferably used.

As the phenyl group substituted by halogen and lower ($C_{1-4}$) alkyl, for example, a 2-fluoro-4-methylphenyl group, a 2-chloro-4-methylphenyl group, a 4-fluoro-2-methylphenyl group and the like are preferably used, and as the phenyl group substituted by halogen and lower ($C_{1-4}$) alkoxy-carbonyl, for example, a 2-chloro-4-methoxycarbonylphenyl group and the like are preferably used, and the phenyl group substituted by halogen and cyano, a 2-chloro-4-cyanophenyl group and the like are preferably used, and as the phenyl group substituted by a halogen and a 5-membered aromatic heterocycle, for example, a 2-fluoro-4-(1H-1,2,4-triazol-1-yl)phenyl group and the like are preferably used, and as the phenyl group substituted by a halogen and a lower ($C_{1-4}$) alkoxy-carbonyl-lower ($C_{1-4}$) alkyl-carbamoyl, such as a 2-chloro-4-(N-tert-butoxycarbonylmethylcarbamoyl)phenyl group, a 2-chloro-4-(N-ethoxycarbonylmethylcarbamoyl)phenyl group and the like are preferably used.

As $Ar^1$, a phenyl group, a halogenophenyl group, a lower ($C_{1-4}$) alkyl-phenyl group, a phenyl group substituted by a halogen and a lower ($C_{1-4}$) alkyl, a phenyl group substituted by a phenyl group substituted by a halogen and a lower ($C_{1-4}$)alkoxy-carbonyl, and the like are preferably used.

As more preferable $Ar^1$, a phenyl group, a phenyl (halogenophenyl) group substituted by 1 to 3 (particularly 1 or 2) halogen atoms (e.g., a 2,3-difluorophenyl group, a 2,3-dichlorophenyl group, a 2,4-difluorophenyl group, a 2,4-dichlorophenyl group, a 2,5-difluorophenyl group, a 2,5-dichlorophenyl group, a 2,6-difluorophenyl group, a 2,6-dichlorophenyl group, a 3,4-difluorophenyl group, a 3,4-dichlorophenyl group, a 3,5-difluorophenyl group, a 3,5-dichlorophenyl group, a 4-bromo-2-fluorophenyl group, a 2-fluorophenyl group, a 2-chlorophenyl group, a 3-fluorophenyl group, a 3-chlorophenyl group, a 4-fluorophenyl group, a 4-chlorophenyl group, a 2-fluoro-4-chlorophenyl group, a 2-chloro-4-fluorophenyl group, a 2,3,4-trifluorophenyl group, a 2,4,5-trifluorophenyl group and the like), a phenyl group substituted by halogen and lower ($C_{1-4}$) alkyl (e.g., a 2-chloro-4-methylphenyl group, a 4-fluoro-2-methylphenyl group and the like), etc. are preferable. Of these, a phenyl (halogenophenyl) group substituted by 1 to 3 (particularly 1 or 2) halogen atoms (e.g., a 2,3-dichlorophenyl group, a 2,4-difluorophenyl group, a 2,4-dichlorophenyl group, a 2,6-dichlorophenyl group, a 2-fluorophenyl group, a 2-chlorophenyl group, a 3-chlorophenyl group, a 2-chloro-4-fluorophenyl group, a 2,4,5-trifluorophenyl group and the like), a phenyl group substituted by halogen and lower ($C_{1-4}$) alkyl (e.g., a 2-chloro-4-methylphenyl group, a 4-fluoro-2-methylphenyl group and the like), and the like are more preferable.

As $Ar^1$, a group represented by the formula

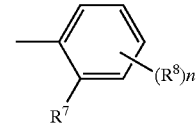

wherein $R^7$ and $R^8$ are the same or different and each is a halogen atom or a lower alkyl group and n is an integer of 0–2, and the like are preferable, and the group wherein at least one of $R^7$ and $R^8$ is a halogen atom is more preferable. As the halogen atom represented by $R^7$ and $R^8$, fluorine atom or chlorine atom is preferable.

As the integer of 1–4 represented by n is preferably 1–3, particularly preferably 2.

As the group represented by the formula

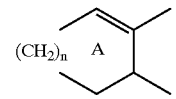

wherein n is as defined above, a group represented by the formula

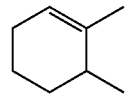

is preferable.

As the substituent that the ring A may have, those similar to the "substituent" of the aforementioned "optionally substituted hydrocarbon group" are used, of which one or two $C_{1-6}$ alkyl groups (e.g., a methyl group, an ethyl group, a propyl group), a $C_{6-14}$ aryl group (e.g., a phenyl group), a halogen atom (e.g., fluorine atom, chlorine atom, bromine atom) and the like are preferable.

Explanation of Partial Structure (C)

As the $C_{1-6}$ alkyl group represented by $R^9$, a methyl group, an ethyl group, a propyl group, an isopropyl group, a butyl group, a isobutyl group, a sec-butyl group, a tert-butyl group, a pentyl group, a hexyl group and the like are used. Of these, a $C_{1-4}$ alkyl group such as a methyl group, an ethyl group, a propyl group, an isopropyl group and the like is preferable, and an ethyl group is particularly preferable.

As the $C_{6-14}$ aryl group represented by $Ar^2$, a phenyl group, a naphthyl group and the like are used, and a phenyl group is preferable. The $C_{6-14}$ aryl group may have 1 to 4 halogen atoms and as the halogen atom, for example, fluorine atom, chlorine atom, bromine atom and iodine atom are used. Of these, fluorine atom, chlorine atom and the like are preferable.

As the $Ar^2$, a phenyl group, a 2,3-difluorophenyl group, a 2,3-dichlorophenyl group, a 2,4-difluorophenyl group, a 2,4-dichlorophenyl group, a 2,5-difluorophenyl group, a 2,5-dichlorophenyl group, a 2,6-difluorophenyl group, a 2,6-dichlorophenyl group, a 3,4-difluorophenyl group, a 3,4-dichlorophenyl group, a 3,5-difluorophenyl group, a 3,5-dichlorophenyl group, a 2-fluorophenyl group, a 2-chlorophenyl group, a 3-fluorophenyl group, a 3-chlorophenyl group, a 4-fluorophenyl group, a 4-chlorophenyl group, a 2-fluoro-4-chlorophenyl group, a 2-chloro-4-fluorophenyl group, a 4-bromo-2-fluorophenyl group, a 2,3,4-trifluorophenyl group, a 2,4,5-trifluorophenyl group, a 2,4,6-trifluorophenyl and the like are specifically used. Of these, a 2,3-dichlorophenyl group, a 2,4-difluorophenyl group, a 2,4-dichlorophenyl group, a 2,6-dichlorophenyl group, a 2-fluorophenyl group, a 2-chlorophenyl group, a 3-chlorophenyl group, a 2-chloro-4-fluorophenyl group, a 2,4,5-trifluorophenyl group and the like are preferable, and a 2-fluoro-4-chlorophenyl group is particularly preferable.

Explanation of (IIIaa)–(IIIff)

As the $C_{6-14}$ aryl group represented by $R^b$, a phenyl group, a naphthyl group and the like are used. Of these, a phenyl group is preferable.

As the $C_{1-6}$ alkanoyl group represented by $R^c$, a formyl group, an acetyl group, an ethylcarbonyl group and the like are used. Of these, an acetyl group is preferable.

As the $C_{1-4}$ alkyl group represented by $R^d$ and $R^e$, a methyl group, an ethyl group, a propyl group, an isopropyl group, a butyl group, an isobutyl group, a sec-butyl group and a tert-butyl group are used. Of these, a methyl group, an ethyl group, a propyl group and the like are preferable, and a methyl group is particularly preferable.

As the $C_{6-14}$ aryl group represented by $R^f$, a phenyl group, a naphthyl group and the like are used. Of these, a phenyl group is preferable.

As the $C_{1-4}$ alkyl group represented by $R^g$, a methyl group, an ethyl group, a propyl group, an isopropyl group, a butyl group, an isobutyl group, a sec-butyl group and a tert-butyl group are used. Of these, a methyl group, an ethyl group, a propyl group and the like are preferable, particularly a methyl group is preferable.

As the $C_{1-6}$ alkyl group represented by $R^h$ and $R^i$, a methyl group, an ethyl group, a propyl group, an isopropyl group, a butyl group, an isobutyl group, a sec-butyl group, a tert-butyl group and the like are used. Of these, a methyl group, an ethyl group, a propyl group and the like are preferably, and a methyl group is particularly preferable.

As the $C_{1-4}$ alkoxy group represented by $R^h$ and $R^i$, a methoxy group, an ethoxy group, a propoxy group and the like are used. Of these, a methoxy group, an ethoxy group and the like are preferable, and a methoxy group is particularly preferable.

As the $C_{1-6}$ alkyl group represented by $R^j$ and $R^k$, a methyl group, an ethyl group, a propyl group, an isopropyl group, a butyl group, an isobutyl group, a sec-butyl group, a tert-butyl group and the like are used. Of these, a methyl group and the like are preferable as $R^j$, and isopropyl group and the like are preferable as $R^k$.

As the $R^aCO-$, for example, a group represented by the formula

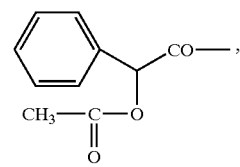

or a group represented by the formula

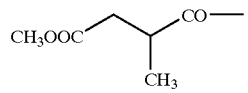

and the like are preferable.

∼∧∧∼ indicates a racemate.

* shows the position of an asymmetric carbon.

As the compound (V) obtained by the production method of the present invention, for example, (1) (6R)-6-({2,4-difluoroanilino}sulfonyl)-1-cyclohexene-1-carboxylic acid ethyl ester, (2) (6R)-6-({2-chloro-4-fluoroanilino}sulfonyl)-1-cyclohexene-1-carboxylic acid ethyl ester and the like are preferable.

The production method of the present invention is explained in the following.

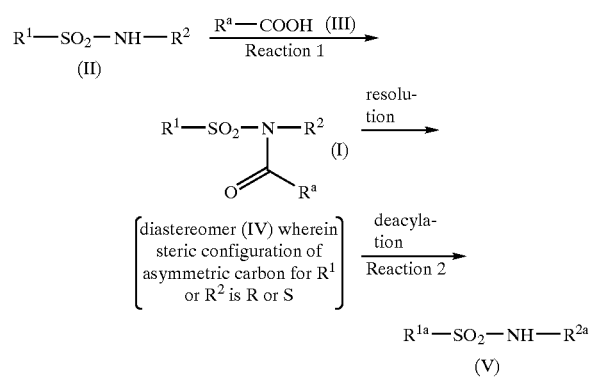

Reaction formula 1

Explanation of Reaction 1

Reaction 1-1

By reacting compound (III), a salt thereof or a reactive derivative thereof with racemate (II) or a salt thereof in the presence or absence of, for example, a base, diastereomeric mixture (I) or a salt thereof can be produced.

(1) Activation of Compound (III) or a Salt Thereof

As a reactive derivative of compound (III) or a salt thereof, for example, an acid halide (e.g., an acid chloride and the like), an acid anhydride and the like are used.

When compound (III) or a salt thereof is activated to give a reactive derivative, for example, a halogen compound (e.g., thionyl chloride, phosphorus trichloride, oxalyl chloride and the like), an alkyl halogenocarbonate (e.g., ethyl chlorocarbonate and the like), an acid chloride substituted by α-polyalkyl (e.g., trimethylacetyl chloride and the like) and the like are used as an activator, of which thionyl chloride and oxalyl chloride are preferable.

As a reaction solvent, for example, aliphatic hydrocarbons such as hexane, heptane and the like; aromatic hydrocarbons such as toluene, xylene and the like; ethers such as THF, diethyl ether and the like; halogenated solvents such as dichloromethane, chloroform and the like; esters such as ethyl acetate and the like; ketones such as acetone, methylethylketone and the like; polar solvents such as acetonitrile and the like; and the like are used, and toluene, THF and the like are preferably used. These solvents may be mixed and used at an arbitrary proportion but may not be used.

The reaction temperature is generally about −50° C.–100° C., preferably about −20–50° C.

The reaction time is generally about 0.1–100 hr, preferably about 0.5–50 hr.

The amount to be used of the compound (III) or a salt thereof is generally about 0.1–10 equivalent amount, preferably about 1–5 equivalent amount relative to the activator.

As the base, for example, organic bases such as triethylamine, pyridine, DBU and the like; inorganic bases such as sodium hydroxide, potassium carbonate and the like; and the like may be used or a base may not be used.

(2) Reaction 1

As the base, for example, an organic base such as triethylamine, pyridine, DBU and the like; an inorganic base such as sodium hydroxide, potassium carbonate and the like; and the like are used, and pyridine is preferably used.

The amount of the base is generally about 0.1–100 equivalent amount, preferably about 1–10 equivalent amount, relative to racemate (II) or a salt thereof.

The reaction solvent, reaction temperature and reaction time are those similar to the aforementioned (1).

The amount of compound (III) or a salt thereof to be used is generally about 0.1–10 equivalent amount, preferably about 1–5 equivalent amount, relative to racemate (II) or a salt thereof.

Reaction 1-2

By reacting compound (III), a salt thereof or a reactive derivative thereof with racemate (II) or a salt thereof in the presence or absence of a base or in the presence or absence of an additive using a condensation agent, a diastereomeric mixture (I) or a salt thereof can be produced.

As the condensation agent, for example, N,N-dicyclohexylcarbodiimide, 1-ethyl-3-(3-dimethylaminopropylcarbodiimide, diethyl cyanophosphate, diphenylphosphorylazide, carbodiimidazole and the like are used.

As the additive, for example, 1-hydroxybenzotriazole, N-hydroxysuccinimide and the like are used.

As the reaction solvent, for example, an aliphatic hydrocarbon such as hexane, heptane and the like; an aromatic hydrocarbon such as toluene, xylene and the like; an ether such as THF, diethyl ether and the like; a halogenated solvent such as dichloromethane, chloroform and the like; an ester such as ethyl acetate; a ketone such as acetone, methyl ethyl ketone and the like; a polar solvent such as acetonitrile, dimethyl sulfoxide, N,N-dimethylformamide, N-methylpyrrolidone and the like; and the like are used. These solvents may be mixed and used at an arbitrary proportion.

The reaction temperature is generally about −10° C.–100° C., preferably about 0–50° C.

The reaction time is generally about 0.1–100 hr, preferably about 0.5–50 hr.

The amount of compound (III) or a salt thereof to be used is generally about 0.1–10 equivalent amount, preferably about 1–5 equivalent amount, relative to racemate (II) or a salt thereof.

As the base, for example, an organic base such as triethylamine, pyridine, DBU and the like; an inorganic base such as sodium hydroxide, potassium carbonate and the like; and the like are used.

The amount of the base is, for example, about 0.1–100 equivalent amount, preferably 1–10 equivalent amount, relative to racemate (II) or a salt thereof.

Explanation of Resolution

The diastereomeric mixture (I) or a salt thereof obtained in reaction 1 is resolved by, for example, solvent extraction, liquid exchange, phase transfer, salting out, crystallization, recrystallization, chromatography and the like to give diastereomer (IV).

Explanation of Reaction 2

The diastereomeric mixture (IV) or a salt thereof obtained in reaction 1 is deacylated to give compound (V) or a salt thereof.

As the reaction solvent, for example, aliphatic hydrocarbons such as hexane, heptane and the like, aromatic hydrocarbons such as toluene, xylene and the like, ethers such as THF, diethyl ether and the like, a halogenated solvent such as dichloromethane, chloroform and the like, esters such as ethyl acetate, ketones such as acetone, methyl ethyl ketone and the like, a polar solvent such as acetonitrile, dimethyl sulfoxide, N,N-dimethylformamide, N-methylpyrrolidone and the like, a primary alcohol such as methanol, ethanol and the like, a secondary alcohol such as isopropyl alcohol, isobutanol and the like, a tertiary alcohol such as tert-butanol, water and the like are used, and an organic solvent-water mixture such as a THF-water mixture and a toluene-water mixture are preferable.

The reaction temperature is generally about −50° C.–100° C., preferably −20° C.–20° C.

The reaction time is generally about 0.1–100 hr, preferably about 0.5–50 hr.

As the base, for example, an organic base such as triethylamine, pyridine, DBU and the like; alkaline metal hydroxides such as sodium hydroxide, lithium hydroxide and the like; alkaline earth metal hydroxides such as barium hydroxide and the like; alkaline metal carbonates such as sodium carbonate, potassium carbonate and the like; alkaline earth metal carbonates such as barium carbonate and the like; inorganic bases such as aqueous ammonia and the like; and the like are used, and sodium hydroxide, potassium hydroxide, barium hydroxide, aqueous ammonia and the like are preferably used.

As the base for the deacylation, barium hydroxide, sodium hydroxide, aqueous ammonia and the like are preferable.

The amount of the base is generally about 0.1–100 equivalent amount, preferably 1–50 equivalent amount, relative to diastereomeric mixture (I) or a salt thereof.

The compounds (I)–(V) may be converted to a salt with an inorganic base, organic base, inorganic acid, organic acid, basic or acidic amino acid, and the like. As a salt with an inorganic base, for example, an alkaline metal salt such as sodium salt, potassium salt, etc.; an alkaline earth metal salt such as calcium salt, magnesium salt, etc.; aluminum salt and ammonium salt, and the like, is used, and, as a salt with an organic base, for example, a salt with trimethylamine, triethylamine, pyridine, picoline, ethanolamine, diethanolamine, triethanolamine, dicyclohexylamine, N,N'-dibenzylethylenediamine, etc. is used. As a salt with an inorganic acid, for example, a salt with hydrochloric acid, hydrobromic acid, nitric acid, sulfuric acid, phosphoric acid, etc. is used, and as a salt with an organic acid, for example, a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. is used. As a salt with a basic amino acid, for example, a salt with arginine, lysine, ornithine, etc. is used, and as a salt with acidic amino acid, for example, a salt with aspartic acid, glutamic acid, and the like, is used.

The racemate (II), a salt thereof, compound (III) and a salt thereof, which are starting material compounds, can be produced according to a method known per se or a similar method.

In the above-mentioned Reaction formula 1, a compound wherein the group represented by the formula $$R^1—SO_2—N—R^2$$

is a group represented by the formula $$\underset{R^4}{\overset{R^3}{\diagdown}}\!\!\sim\!\!SO_2—N—Ar \quad (A)$$

wherein each symbol is as defined above, is used, the following Reaction formula 2 applies.

Reaction Formula 2

Reaction formula 2

(IIa) → [R$^a$—COOH (III), Reaction 1] → (Ia) → [resolution] → (IVa) → [deacylation, Reaction 2] → (Va)

wherein each symbol is as defined above.

In the above-mentioned Reaction formula 1, when a compound wherein the group represented by the formula $$R^1—SO_2—N—R^2$$

is a group represented by the formula (B)

wherein each symbol is as defined above, is used, the following Reaction formula 3 applies.

Reaction Formula 3

(IIb) → [R$^a$—COOH (III), Reaction 1] → (Ib) → [resolution] → (IVb) → [deacylation, Reaction 2] → (Vb)

wherein each symbol is as defined above.

In the above-mentioned Reaction formula 1, when a compound wherein the group represented by the formula $$R^1—SO_2—N—R^2$$

is a group represented by the formula (C)

wherein each symbol is as defined above, is used, the following Reaction formula 4 applies.
Reaction Formula 4

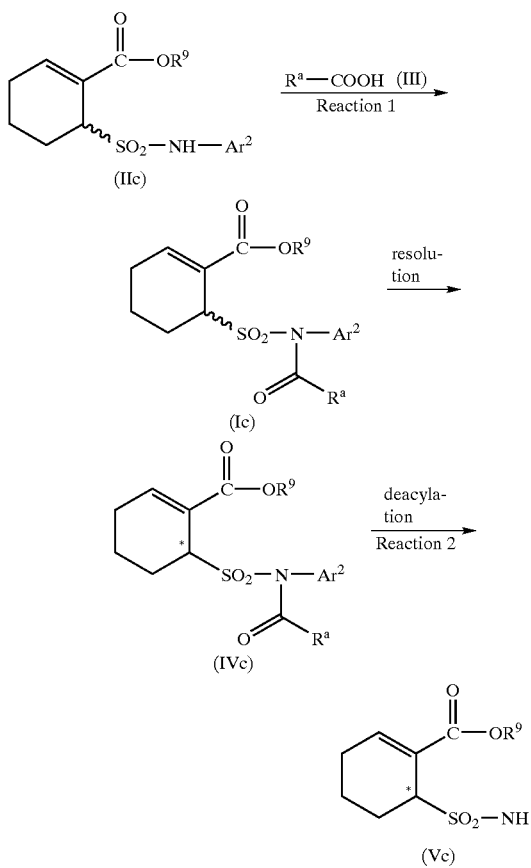

wherein each symbol is as defined above.

The above-mentioned Reaction formula 2–4 can be carried out under the same conditions as for Reaction formula 1.

The compound represented by the formula which is used for the production method of the present invention

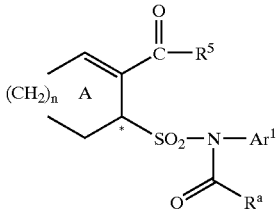

(IVb)

wherein each symbol is as defined above, or a salt thereof is a novel compound.

In the present invention, optically active compound (V) and a salt thereof can be also produced by the action of hydrolase on diastereomeric mixture (I) or a salt thereof.

As the hydrolase to be used for the hydrolysis reaction, hydrolase derived from microorganisms, such as bacteria (the genera *Pseudomonas, Streptomyces, Bacillus, Acetobacter* and *Alcaligenes*), fungus (the genera *Candida* and *Trichosporon*), animal cell (pig hepatic cell, pig pancreatic cell) and the like is used.

As the hydrolase, a culture product of a microorganism can be used as it is, but where necessary, purification may be applied. For example, for isolation of hydrolase from bacteria, the following steps can be applied according to a method known per se.

1) Bacteria is cultured by a conventional method to give a culture broth, which is subjected to centrifugal separation to give a culture supernatant and a fungus body.

2) The fungus body disrupted by ultrasonication, French press, alumina crushing, fungus body enzyme treatment and the like and separated by centrifugation to give a cell extract.

3) The above-mentioned culture supernatant and cell extract are subjected to precipitation with organic solvent, fractionation with ammonium sulfate, ion exchange chromatography, adsorption chromatography, gel permeation, affinity chromatography and the like to give a purified product of esterase. The esterase to be used for this reaction may be an unpurified product, a partially purified product or a purified single product. This esterase may be used as it is or may be immobilized on a suitable carrier. As the carrier, for example, polysaccharide derivatives such as cellulose and the like, amino acid copolymer, synthetic polymer, activated carbon, porous glass, diatomaceous earth, alumina, silica gel and the like are used.

As the hydrolase, for example, carboxy esterase, allyl esterase, choline esterase, lipase and the like are used, with preference given to lipase. For example, a lipase derived from bacteria such as the genera *Pseudomonas, Alcaligenes* and the like is used.

As the hydrolase to be used in the present invention, a commercially available product can be used. For example, PS, PS-D and PS-C (derived from the genus *Pseudomonas,* produced by Amano Pharmaceutical Co., Ltd.), AK-20 (derived from the genus *Pseudomonas,* produced by Amano Pharmaceutical Co., Ltd.), AH (derived from the genus *Pseudomonas,* produced by Amano Pharmaceutical Co., Ltd.), Lipase QL, QLC, QLG (derived from the genus *Alcaligenes,* produced by Meito Sangyo Co., Ltd.) and the like are preferably used.

This hydrolysis reaction is characterized by deacylation of one acyl moiety on a carboxy of the optically active form of the diastereomeric mixture (I) or a salt thereof, which is more rapid than the deacylation of the other. As a result, a mixture of the deacylated optically active compound (V) or a salt thereof and the non-deacylated diastereomer or a salt thereof is obtained. They both can be isolated and purified by a method known per se, such as solvent extraction, liquid exchange, phase transfer, salting out, crystallization, recrystallization and chromatography and separated.

In the hydrolysis reaction, the amount of the hydrolase to be used varies depending on the kind thereof, form (e.g., immobilization) and the like, and is not particularly limited. However, it is about 0.001-fold to about 100-fold, preferably about 0.1-fold to about 10-fold (all in by weight), relative to diastereomeric mixture (I) or a salt thereof.

The reaction temperature is generally about 0° C.–about 80° C., preferably about 15° C.–about 50° C., more preferably about 15° C.–35° C.

The reaction time is generally about 10 min–about 100 hr, preferably about 1 hr–about 72 hr.

The hydrolysis reaction may be carried out in the presence of, for example, an additive such as an enzyme stabilizer, a water substitute (e.g., ethylene glycol) and the like.

The hydrolysis reaction proceeds both in water and an organic solvent. As the organic solvent, for example, a hydrocarbon solvent (e.g., hexane, pentane, cyclohexane and the like), an amide solvent (e.g., N,N-dimethylformamide (DMF), N,N-dimethylacetamide, N-methylpyrrolidone and the like), an aromatic hydrocarbon solvent (e.g., toluene, benzene, chlorobenzene and the like), an aliphatic ester solvent (ethyl acetate, propyl acetate, butyl acetate and the like), an ether solvent (diisopropyl ether, tert-butylmethyl ether, diethyl ether, tetrahydrofuran, 1,4-dioxane, 1,2-dimethoxyethane and the like), a halogenated hydrocarbon solvent (chloroform, dichloromethane, 1,2-dichloroethane, carbon tetrachloride), an alcohol solvent (methanol, ethanol, isopropanol, tert-butanol and the like), a ketone solvent (e.g., acetone, methyl ethyl ketone and the like), a sulfoxide solvent (e.g., dimethyl sulfoxide and the like), a nitrile solvent (e.g., acetonitrile, propionitrile and the like) and the like are exemplified. These solvents may be used alone or used as a mixed solvent. Preferably, diisopropyl ether, tert-butylmethyl ether, tetrahydrofuran, acetone, acetonitrile and the like are used.

In the hydrolysis reaction, the concentration of diastereomeric mixture (I) or a salt thereof is about 0.1%–about 50%, preferably about 1%–about 30%.

For advantageous progress of this reaction, addition of water or alcohol is effective. When water is added, a hydrolysis reaction proceeds and when alcohol is added, alcoholysis proceeds.

As the alcohol, methanol, ethanol, propanol, butanol, 2-chloroethanol and the like are used, and methanol and ethanol are particularly preferable.

The amount of water and alcohol to be added is free of particular limitation and it is about 0.1% by volume–about 100% by volume, preferably about 1% by volume–about 20% by volume, relative to the solvent.

In addition, an additive may be added to water to give a buffer, and the reaction may be carried out under control of pH. As the additive, for example, disodium hydrogen phosphate and sodium dihydrogen phosphate, tris(hydroxymethyl)aminomethane and hydrochloric acid, tris(hydroxymethyl)aminomethane and sodium hydroxide, citric acid and sodium citrate, acetic acid and sodium acetate, citric acid and disodium hydrogen phosphate, glycine and sodium hydroxide, sodium carbonate and sodium hydrogencarbonate and the like are used.

In the hydrolysis reaction, the amount of hydrolase to be used is not particularly limited, because it varies depending on the kind and the form (e.g., immobilization) and the like, but it is generally about 0.001-fold to 100-fold, preferably 0.1-fold–10-fold amount (all in weight) relative to diastereomeric mixture (I) or a salt thereof.

The hydrolysis reaction may be any of standing still, shaking and stirring. When esterase is immobilized on a carrier, the reaction may be carried out in a bioreactor.

As mentioned above, optically active compound (V) or a salt thereof can be obtained by a method comprising resolution of diastereomeric mixture (I) or a salt thereof to give a diastereomer or a salt thereof, and then deacylation thereof to give optically active compound (V) or a salt thereof, or a method comprising reaction of diastereomeric mixture (I) or a salt thereof with hydrolase to give a mixture of diastereomer or a salt thereof and optically active compound (V) or a salt thereof, separation of optically active compound (V) or a salt thereof from the mixture, deacylation of the remaining diastereomer or a salt thereof to convert the obtained compound to optically active compound (V). In the present invention, the former method without using hydrolase is preferable.

Of the compounds (V) obtained by the production method of the present invention, a compound represented by the formula

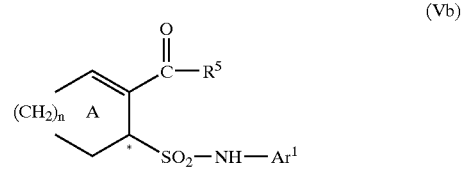

(Vb)

wherein each symbol is as defined above, or a prodrug of a salt thereof refers to a compound which is converted to compound (Vb) under a physiological condition in vivo as a result of a reaction with an enzyme, gastric acid etc., thus a compound undergoing an enzymatic oxidation, reduction, hydrolysis etc. to convert into compound (Vb) and a compound subjected to hydrolysis and the like by gastric acid etc. to convert to compound (Vb). A prodrug for compound (V) may be a compound obtained by subjecting an amino group in compound (Vb) to an acylation, alkylation or phosphorylation (e.g., a compound obtained by subjecting an amino group in compound (Vb) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation, etc.); a compound obtained by subjecting a hydroxy group in compound (Vb) to an acylation, alkylation, phosphorylation and boration (e.g., a compound obtained by subjecting a hydroxy group in compound (Vb) to an acetylation, palmitoylation, propanoylation, pivaloylation, succinylation, fumarylation, alanylation, dimethylaminomethylcarbonylation, etc.); a compound obtained by subjecting a carboxyl group in compound (Vb) to an esterification or amidation (e.g., a compound obtained by subjecting a carboxyl group in compound (Vb) to an ethylesterification, phenylesterification, carboxymethylesterification, dimethylaminomethylesterification, pivaloyloxymethylesterification, ethoxycarbonyloxyethylesterification, phthalidylesterification, (5-methyl-2-oxo-1,3-dioxolen-4-yl)methylesterification, cyclohexyloxycarbonylethylesterification and methylamidation, etc.) and the like. Any of these compounds can be produced from compound (Vb) by a method known per se.

A prodrug for compound (Vb) may also be one which is converted to compound (Vb) under a physiological condition, such as those described in "IYAKUHIN no KAIHATSU (Development of Pharmaceuticals)", Vol. 7, *Design of Molecules*, p.163–198, Published by HIROKAWA SHOTEN (1990).

The compound (Vb), a salt thereof and a prodrug thereof may be a hydrate or non-hydrate.

The compound (Vb), a salt thereof and a prodrug thereof may be labeled with an isotope (e.g., $^3$H, $^{14}$C, $^{35}$S, $^{125}$I etc.) and the like.

The compound (V) or a salt thereof or a prodrug thereof obtained by the production method of the present invention can be used as a pharmaceutical product, agrochemical, food, cosmetic, chemical product and the like, based on the action it has.

For example, compound (Vb) or a salt thereof or a prodrug thereof is safe for human administration as a phannaceutical agent (e.g., prophylactic or therapeutic agent for various diseases), as an animal medicine and the like for other manunals (e.g., rat, mouse, guinea pig, monkey, cat, cattle, dog, horse, goat, pig, and the like).

Since compound (Vb), a salt thereof and a prodrug thereof have low toxicity, a nitric oxide (NO) production-inhibitory effect and an inhibitory effect on the production of an inflammatory cytokine such as TNF-α, IL-1, IL-6, etc., the pharmaceutical composition, which contains compound (Vb), a salt thereof or a prodrug thereof is useful as a therapeutic and/or prophylactic agent in a mammal (e.g., rat, mouse, guinea pig, monkey, cat, cattle, dog, horse, goat, pig, human and the like) against diseases such as cardiac disease, autoimmune disease, inflammatory disease, central nervous system disease, infectious disease, sepsis, septic shock and the like, including, for example, ichorrhemia, endotoxin shock, exotoxin shock, cardiac deficiency, shock, hypotension, rheumatoid arthritis, osteoarthritis, gastritis, ulcerative colitis, peptic ulcer, stress-induced gastric ulcer, Crohn's disease, autoimmune disease, post-transplant tissue failure and rejection, postischemic re-perfusion failure, acute coronary microvascular embolism, shock-induced vascular embolism (disseminated intravascular coagulation (DIC) and the like), ischemic cerebral disorder, arterial sclerosis, pernicious anemia, Fanconi's anemia, drepanocythemia, pancreatitis, nephrose syndrome, nephritis, renal failure, insulin-dependent diabetes, insulin-independent diabetes, hepatic porphyria, alcoholism, Parkinson's disease, chronic leukemia, acute leukemia, tumor, myeloma, side effects caused by anticancer agents, infantile and adult respiratory distress syndrome, pulmonary emphysema, dementia, Alzheimer's disease, multiple sclerosis, vitamin E deficiency, aging, sunburn, muscular dystrophy, myocarditis, cardiomyopathy, myocardial infarction, myocardial post-infarction syndrome, osteoporosis, pneumonia, hepatitis, psoriasis, pain, cataract, influenza infection, malaria, human immunodeficiency virus (HIV) infection, radiation hazard, burn, hypercalcemia, tonic spondylitis, osteopenia, bone Behcet's disease, osteomalacia, fracture, acute bacterial meningitis, *Helicobactor pylon* infection, invasive staphylococcal infection, tuberculosis, systemic mycosis, herpes simplex virus infection, varicella-herpes zoster virus infection, human papilloma virus infection, acute viral encephalitis, encephalitis, asthma, atopic dermatitis, allergic rhinitis, reflux esophagitis, fever, hyper cholesteremia, hyperglycemia, hyperlipidemia, diabetic complication, diabetic renal disease, diabetic neuropathy, diabetic retinopathy, gout, gastric atony, hemorrhoid, systemic lupus erythematosus, spinal damage, insomnia, schizophrenia, epilepsy, cirrhosis, hepatic failure, instable angina, valvular disease, dialysis-induced thrombocytopenia, acute ischemic cerebral apoplexy, acute cerebral thrombosis, cancer metastasis, urinary bladder cancer, mammary cancer, uterine cervical cancer, colon cancer, gastric cancer, ovarian cancer, prostatic cancer, parvicellular pulmonary cancer, non-parvicellular pulmonary cancer, malignant melanoma, Hodgkin's disease, non-Hodgkin lymphoma and the like, or as a pharmaceutical agent for efficient in vitro fertilization (WO99/46242).

Best Mode for Embodying the Invention

The present invention is explained in more detail in the following Examples which are not to be construed as limiting. In the following Examples, the term "recrystallized" is used interchangeably to mean "recrystallization".

EXAMPLE 1

Production of (6R)-6-({[(2S)-2-(acetyloxy)-2-phenylethanoyl]-2-chloro-4-fluoroanilino}sulfonyl)-1-cyclohexene-1-carboxylic Acid Ethyl Ester (Compound 3)

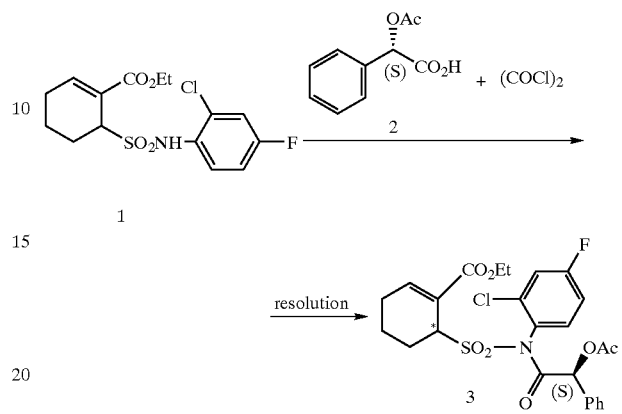

Compound 2 (1.94 g) was dissolved in toluene (30 ml), DMF (0.03 ml) was added and oxalyl chloride (1.7 ml) was added dropwise under ice-cooling. The mixture was stirred at room temperature for 1 hr and the reaction solution was cooled to −15° C. and compound 1 (1.81 g) was added. Pyridine (3.5 ml) was added dropwise and the mixture was stirred at the same temperature for 2 hr. After the completion of the reaction, water (15 ml) was added and the mixture was partitioned. The organic layer was washed successively with 2N hydrochloric acid (15 ml), water (15 ml)×3 and saturated brine (15 ml), and the solvent was evaporated. IPA (6 ml) was added to the obtained oily substance (3 g) and dissolved by heating, after which the solution was allowed to crystallize at 40° C. and stirred at the same temperature for 1 hr. After aging at room temperature for 1 hr, the crystals were collected by filtration to give the title compound (1.06 g) as white crystals. yield 39%, 98% de. $^1$H-NMR (300 MHz, CDCl$_3$, δ): 1.24 (3H, t, J=7.1 Hz), 1.70–1.95 (3H, m), 2.05–2.30 (4H, m), 2.35–2.45 (1H, m), 3.06 (1H, bd, J=14.2 Hz), 4.19 (2H, q, J=7.1 Hz), 5.20 (1H, bd, J=3.9 Hz), 5.66 (1H, s), 6.95–7.00 (2H, m), 7.05–7.15 (1H, m), 7.20–7.35 (5H, m), 8.02 (1H, dd, J=8.9, 5.7 Hz).

Anal for C$_{25}$H$_{25}$NO$_7$SClF Calcd. (%): C, 55.81; H, 4.68; N, 2.60; S, 5.96; Cl, 6.59; F, 3.53; O, 20.82. Found (%): C, 55.85; H, 4.38; N, 2.62; S, 5.92; Cl, 6.71; F, 3.23.

EXAMPLE 2

Production of (6R)-6-({2-chloro-4-fluoroanilino}sulfonyl)-1-cyclohexene-1-carboxylic acid ethyl ester (Compound 4)

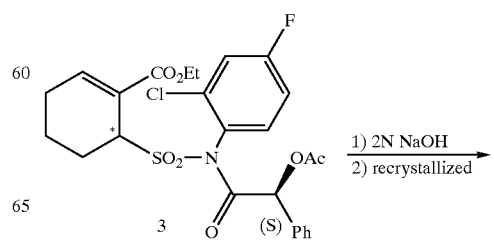

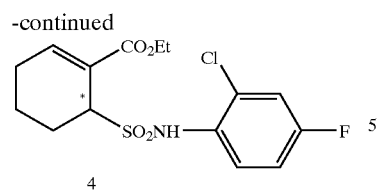

4

(1) Deacylation

A 2N sodium hydroxide (280 ml)-THF (280 ml) solution was ice-cooled and compound 3 (30 g) was added at 0° C. The mixture was stirred at the same temperature for 2 hr. After the completion of the reaction, pH was adjusted to around 4 with 1N hydrochloric acid (about 250 ml) and ethyl acetate (140 ml) was added to partition the mixture. The aqueous layer was extracted with ethyl acetate (250 ml). The combined organic layer was washed with saturated aqueous sodium hydrogencarbonate (250 ml) and 10% brine (250 ml) and the solvent was evaporated. IPE-cyclohexane (1:4) (60 ml) was added to the obtained oily substance (20 g) and dissolved by heating. The solution was stirred at room temperature for 30 min and the seed crystal was added. The mixture was further stirred for 30 min. After stirring under ice-cooling for 1.5 hr, the mixture was filtrated and washed with cold cyclohexane (20 ml) to give crystals. Drying in vacuo at 40° C. gave a crude substance (15.0 g) as white crystals. yield 74%, 93% ee.

(2) Recrystallization

The crude substance (3 g) was dissolved in IPA (15 ml) by heating and the solution was stirred at room temperature for 15 hr. The precipitated crystals were collected by filtration and washed with IPA (3 ml). The mother liquor was heated to 60° C. and heptane (18 ml) was added. After stirring at room temperature for 30 min, the seed crystal was added. The mixture was cooled and stirred at 0° C. for 2 hr. The crystals were collected by filtration, washed with cold heptane (10 ml) and dried in vacuo at 40° C. to give the title compound (2.05 g) as white crystals. yield 68%, 99% ee.

$^1$H-NMR (300 MHz, CDCl$_3$, δ): 1.24 (3H, t, J=7.1 Hz), 1.69–1.78 (2H, m), 2.16–2.30 (2H, m), 2.41–2.55 (2H, m), 4.15 (2H, q, J=7.1 Hz), 4.71 (1H, bd, J=4.7 Hz), 6.9.6–7.00 (2H, m), 7.12–7.16 (1H, m), 7.28–7.31 (1H, m), 7.69 (1H, dd, J=9.1, 5.3 Hz). Anal for C$_{15}$H$_{17}$NO$_4$SClF Calcd. (%): C, 49.79; H, 4.74; N, 3.87; S, 8.86; Cl, 9.80; F, 5.25; O, 17.69. Found (%): C, 49.71; H, 4.67; N, 3.90; S, 8.80; Cl, 9.87; F, 5.22.

EXAMPLE 3

Production of (6R)-6-({2-chloro-4-fluoro[(2R)-4-methoxy-3-methyl-4-oxobutanoyl]anilino}sulfonyl)-1-cyclohexene-1-carboxylic acid ethyl ester (Compound 6)

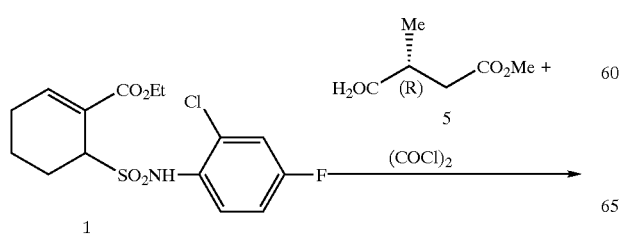

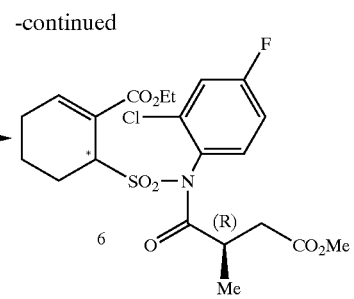

Compound 5 (1.46 g) was dissolved in THF (8 ml), DMF (0.03 ml) was added and oxalyl chloride (0.96 ml) was added dropwise under ice-cooling. The mixture was stirred at room temperature for 30 min and compound 1 (1.81 g) was added. Triethylamine (3.1 ml) and pyridine (0.89 ml) were added dropwise and the mixture was stirred at the same temperature for 30 min. After the completion of the reaction, water (15 ml) and ethyl acetate (15 ml) were added and the mixture was partitioned. The organic layer was washed successively with 1N hydrochloric acid (15 ml), water (15 ml)×3 and saturated brine (15 ml), and the solvent was evaporated. Methanol (4.5 ml) was added to the obtained oily substance, and after refluxing, the mixture was allowed to cool to room temperature and stirred under ice-cooling for 30 min. The crystals were collected by filtration to give the title compound (1.01 g) as white crystals. yield 41%, 97% de.

$^1$H-NMR (300 MHz, CDCl$_3$, δ): 1.12 (3H, d, J=2.3 Hz), 1.26 (3H, t, J=7.1 Hz), 1.76–1.85 (2H, m), 1.90–2.05 (1H, m), 2.15–2.50 (3H, m), 2.60–2.70 (1H, m), 2.80–2.99 (1H, m), 3.03 (1H, bd, J=12.9 Hz), 3.68 (3H, s), 4.19 (2H, q, J=7.1 Hz), 5.20 (1H, bs), 7.04–7.10 (1H, m), 7.24–7.10 (2H, m), 7.80 (1H, dd, J=8.9, 5.7 Hz). Anal for Anal for C$_{21}$H$_{25}$NO$_7$SClF Calcd. (%): C, 51.48; H, 5.14; N, 2.86; S, 6.54; Cl, 7.24; F, 3.88; O, 22.86. Found (%): C, 51.40; H, 5.27; N, 2.83; S, 6.38; Cl, 7.29; F, 3.67.

EXAMPLE 4

Production of (6R)-6-({2-chloro-4-fluoroanilino}sulfonyl)-1-cyclohexene-1-carboxylic acid ethyl ester (Compound 4)

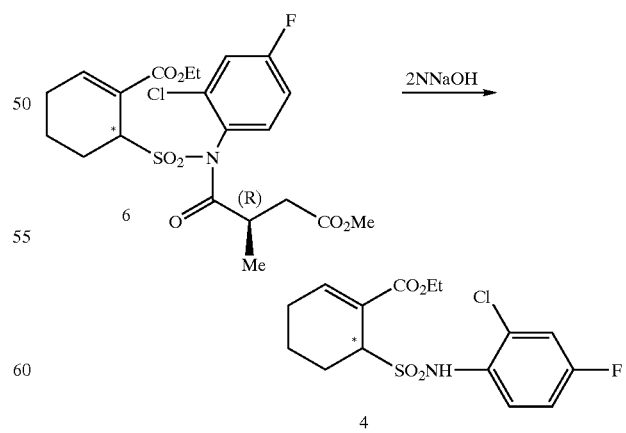

Barium hydroxide octahydrate (0.59 g) and compound 6 (100 mg) were suspended in THF-water (1:1, 2 ml) and the mixture was stirred for 4 hr. After the completion of the reaction, pH was adjusted to around 4 with 1N hydrochloric acid. Ethyl acetate (10 ml) was added for partitioning. The organic layer was washed with saturated aqueous sodium hydrogencarbonate (10 ml) and 10% brine (10 ml) and the solvent was evaporated to give the title compound (22.6 mg) as an oily substance. yield 31%, 69% ee.

EXAMPLE 5

(6S)-6-({[(2R)-2-(Acetyloxy)-2-phenylethanoyl]-2-chloro-4-fluoroanilino}sulfonyl)-1-cyclohexene-1-carboxylic acid ethyl ester (Compound 9)

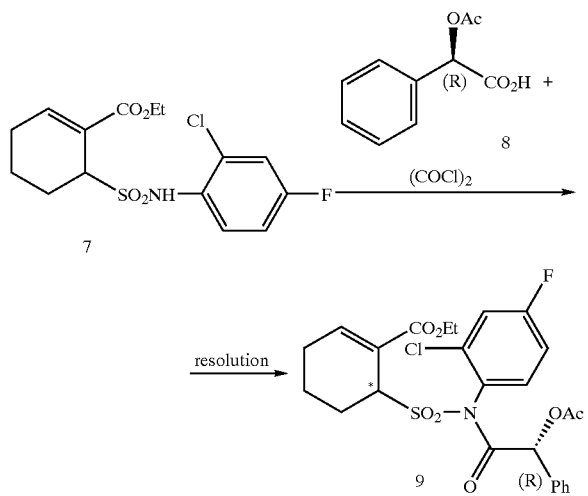

Compound 8 (9.7 g) was dissolved in toluene (150 ml), DMF (0.5 ml) was added and oxalyl chloride (8.7 ml) was added dropwise under ice-cooling. The mixture was stirred at room temperature for 1 hr and the reaction solution was cooled to −15° C. Compound 7 (9.04 g) was added and pyridine (17.8 ml) was added dropwise. The mixture was stirred at the same temperature for 2 hr. After the completion of the reaction, water (80 ml) was added and the mixture was partitioned. The organic layer was washed successively with 2N hydrochloric acid (80 ml), water (80 ml)×3 and saturated brine (80 ml), and the solvent was evaporated. IPA (45 ml) was added to the obtained oily substance, and dissolved by heating. The crystals were allowed to precipitate at 40° C. and the mixture was stirred at the same temperature for 1 hr. After aging at room temperature for 1 hr, the crystals were collected by filtration to give the title compound (3.35 g) as white crystals. yield 25%, 98% de.

$^1$H-NMR (300 MHz, CDCl$_3$, δ): 1.23 (3H, t, J=7.1 Hz), 1.70–2.00 (3H, m), 2.15–2.35 (4H, m), 2.40–2.50 (1H, m),3.10 (1H, bd, J=14.2 Hz), 4.22 (2H, q, J=7.1 Hz), 5.21 (1H, bs), 5.68 (1H, s), 6.98–7.00 (2H, m), 7.10–7.20 (1H, m), 7.25–7.40 (5H, m), 8.03 (1H, dd, J=8.9, 5.7 Hz). Anal for C$_{25}$H$_{25}$NO$_7$SClF Calcd. (%): C, 55.81; H, 4.68; N, 2.60; S, 5.96; Cl, 6.59; F, 3.53; O, 20.82. Found (%): C, 55.76; H, 4.42; N, 2.53; S, 5.73; Cl, 6.63; F, 3.60.

EXAMPLE 6

(6S)-6-({2-Chloro-4-fluoroanilino}sulfonyl)-1-cyclohexene-1-carboxylic acid ethyl ester (Compound 11)

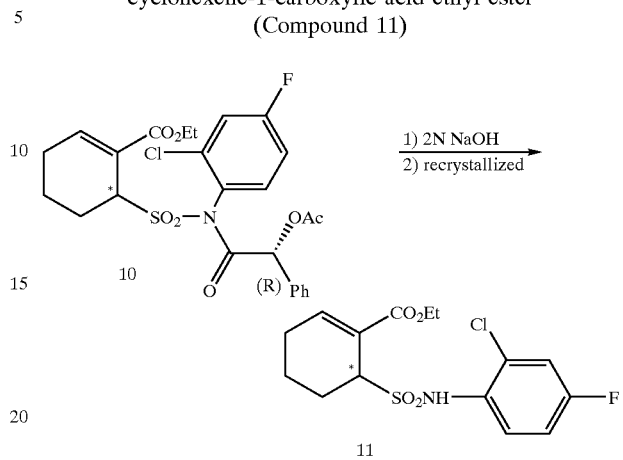

1) Deacylation→2) Recrystallization

A 2N sodium hydroxide (18.5 ml)-THF (18.5 ml) solution was ice-cooled and compound 10 (2 g) was added at 0° C. The mixture was stirred at the same temperature for 2 hr. After the completion of the reaction, pH was adjusted to around 4 with 1N hydrochloric acid (about 18 ml) and ethyl acetate (10 ml) was added to partition the mixture. The aqueous layer was extracted with ethyl acetate (10 ml). The combined organic layer was washed with saturated aqueous sodium hydrogencarbonate (10 ml) and 10% brine (10 ml) and the solvent was evaporated. IPE (2 ml) was added to the obtained oily substance (1.5 g) and dissolved by heating. The solution was stirred at room temperature and then under ice-cooling. The precipitated crystals were collected by filtration, and washed with IPE (1 ml). The mother liquor was heated to 60° C. and stirred at room temperature for 1 hr and at 0° C. for 30 min. The crystals were collected by filtration and washed with cold IPE (2 ml). Drying in vacuo at 40° C. gave the title compound (687 mg) as white crystals. yield 51%, 97% ee.

$^1$H-NMR (300 MHz, CDCl$_3$, δ): 1.24 (3H, t, J=7.1 Hz), 1.70–1.85 (2H, m), 2.16–2.35 (2H, m), 2.42–2.60 (2H, m), 4.15 (2H, q, J=7.1 Hz), 4.61 (1H, bd, J=5.0 Hz), 6.97–7.05 (2H, m), 7.13–7.20 (1H, m), 7.30–7.35 (1H, m), 7.69 (1H, dd, J=9.1, 5.3 Hz). Anal for C$_{15}$H$_{17}$NO$_4$SClF Calcd. (%): C, 49.79; H, 4.74; N, 3.87; S, 8.86; Cl, 9.80; F, 5.25; O, 17.69. Found (%): C, 49.62; H, 4.36; N, 3.82; S, 8.66; Cl, 9.46; F, 5.24.

INDUSTRIAL APPLICABILITY

According to the production method of the present invention, an optically active compound (V) or a salt thereof can be produced conveniently and efficiently. Accordingly, the production method of the present invention is highly useful for industrial production.

This application claims priority to Japanese patent application No. 2000-323309, the contents of which are incorporated by reference in the present specification. The references cited herein, including patents and patent applications, are hereby incorporated by reference in their entireties, to the extent that they have been disclosed herein.

What is claimed is:

1. A method comprising
reacting a racemate represented by the formula $$R^1-SO_2-NH-R^2 \quad (II)$$

wherein
R$^1$ and R$^2$ are the same or different and each is an optionally substituted hydrocarbon group or an optionally substituted heterocyclic group, and only one of R$^1$ and R$^2$ contains one asymmetric carbon, or a salt thereof with an optically active compound represented by the formula $$R^a-COOH \quad (III)$$

wherein
R$^a$ is an optically active and optionally substituted hydrocarbon group or an optically active and optionally substituted heterocyclic group, a salt thereof or a reactive derivative thereof to give a diastereomeric mixture represented by the formula

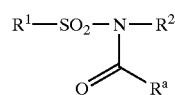

wherein each symbol is as defined above,
or a salt thereof, and
resolving the diastereomeric mixture or a salt thereof
wherein resolution is carried out by solvent extraction, liquid exchange, phase transfer, salting out, crystallization, recrystallization or chromatography,
to produce the diastereomer having a steric configuration of the asymmetric carbon for R$^1$ or R$^2$ of an R configuration or an S configuration,
or a salt thereof.

2. The method of claim 1, wherein R$^a$ is an optically active and optionally substituted hydrocarbon group containing an asymmetric carbon or an optically active and optionally substituted heterocyclic group containing an asymmetric carbon.

3. The method of claim 1, wherein the resolution is free of hydrolase.

4. A production method of a diastereomeric mixture represented by the formula

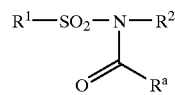

wherein R$^1$ and R$^2$ are the same or different and each is an optionally substituted hydrocarbon group or an optionally substituted heterocyclic group, and only one of R$^1$ and R$^2$ contains one asymmetric carbon, and R$^a$ is an optically active and optionally substituted hydrocarbon group or an optically active and optionally substituted heterocyclic group, or a salt thereof, which comprises reacting a racemate represented by the formula $$R^1-SO_2-NH-R^2 \quad (II)$$

wherein each symbol is as defined above, or a salt thereof with an optically active compound represented by the formula $$R^a-COOH \quad (III)$$

wherein R$^a$ is as defined above, or a salt thereof or a reactive derivative thereof.

5. A production method of an optically active compound represented by the formula $$R^{1a}-SO_2-NH-R^{2a} \quad (V)$$

wherein R$^{1a}$ and R$^{2a}$ are the same or different and each is an optically substituted hydrocarbon group or an optionally substituted heterocyclic group, only one of R$^{1a}$ and R$^{2a}$ contains one asymmetric carbon, and a steric configuration of the asymmetric carbon is an R configuration or an S configuration, or a salt thereof, which comprises reacting a racemate represented by the formula $$R^1-SO_2-NH-R^2 \quad (II)$$

wherein R$^1$ and R$^2$ are the same or different and each is an optionally substituted hydrocarbon group or an optionally substituted heterocyclic group and only one of R$^1$ and R$^2$ contains one asymmetric carbon, or a salt thereof with an optically active compound represented by the formula $$R^a-COOH \quad (III)$$

wherein R$^a$ is an optically active and optionally substituted hydrocarbon group or an optically active and optionally substituted heterocyclic group, a salt thereof or a reactive derivative thereof to give a diastereomeric mixture represented by the formula

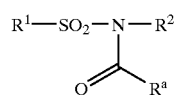

wherein each symbol is as defined above, or a salt thereof,
resolving the diastereomeric mixture or a salt thereof, wherein said resolution is carried out by solvent extraction, liquid exchange, phase transfer, salting out, crystallization, recrystallization or chromatography,
to give the diastereomer wherein the asymmetric carbon for R$^1$ or R$^2$ has a steric configuration of an R configuration or an S configuration or a salt thereof,
then deacylating said diastereomer or a salt thereof.

6. The method of claim 1, wherein the group represented by the formula

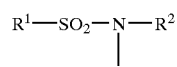

is a group represented by the formula

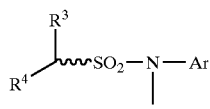 (A)

wherein R³ and R⁴ are the same or different and each is an optionally substituted hydrocarbon group or an optionally substituted heterocyclic group, R³ and R⁴ may form an optionally substituted cyclic group together with the adjacent carbon atom, Ar is an optionally substituted hydrocarbon group or an optionally substituted heterocyclic group, and the symbol ⌇ indicates a racemate, and the diastereomer comprises a group represented by the formula

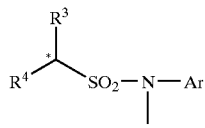 (A')

wherein * shows the position of the asymmetric carbon and other symbols are as defined above, which has a steric configuration of the asymmetric carbon of an R configuration or an S configuration.

7. The method of claim 1, wherein the group represented by the formula

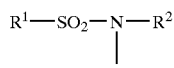

is a group represented by the formula

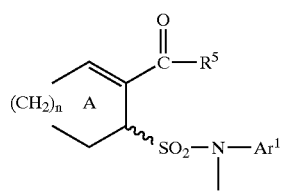 (B)

wherein R⁵ is an optionally substituted hydrocarbon group, an optionally substituted heterocyclic group, the formula —OR⁶ (R⁶ is a hydrogen atom or an optionally substituted aliphatic hydrocarbon group) or the formula —NR⁷R⁸ (R⁷ and R⁸ are the same or different and each is a hydrogen atom or an optionally substituted aliphatic hydrocarbon group), Ar¹ is an optionally substituted aromatic hydrocarbon group, ring A may be further substituted, n is an integer of 1–4 and the symbol ⌇ indicates a racernate, and the diastereomer comprises a group represented by the formula

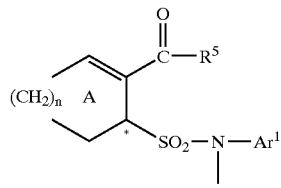 (B')

wherein * shows the position of the asymmetric carbon and other symbols are as defined above, which has a steric configuration of the asymmetric carbon of an R configuration or an S configuration.

8. The method of claim 1, wherein the group represented by the formula

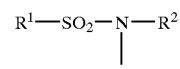

is a group represented by the formula

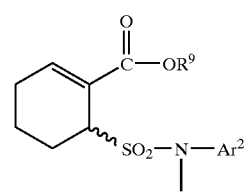 (C)

wherein R⁹ is a $C_{1-6}$ alkyl group, Ar² is a $C_{6-14}$ aryl group optionally having a halogen atom, and the symbol ⌇ indicates a racemate, and the diastereomer comprises a group represented by the formula

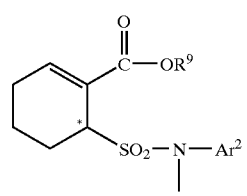 (C')

wherein * shows the position of the asymmetric carbon and other symbols are as defined above, which has a steric configuration of the asymmetric carbon of an R configuration or an S configuration.

9. The method of claim 4, wherein the compound represented by the formula

$R^a$—COOH      (III)

wherein $R^a$ is an optically active and optionally substituted hydrocarbon group or an optically active and optionally substituted heterocyclic group, is a compound containing an asymmetric carbon at the α-position of the carboxyl group.

10. The method of claim 9, wherein the compound represented by the formula

$R^a$—COOH      (III)

wherein $R^a$ is an optically active and optionally substituted hydrocarbon group or an optically active and optionally substituted heterocyclic group is (1) an optically active compound represented by the formula

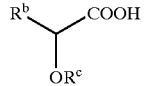
(IIIa)

wherein $R^b$ is a $C_{6-14}$ aryl group and $R^c$ is a $C_{1-6}$ alkanoyl group or a $C_{1-4}$ alkyl group, or a salt thereof, or (2) an optically active compound represented by the formula

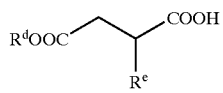
(IIIb)

wherein $R^d$ and $R^e$ are the same or different and each is a $C_{1-4}$ alkyl group, or a salt thereof.

11. A compound represented by the formula

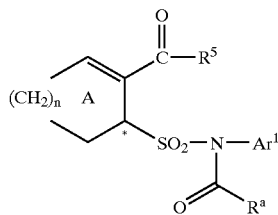
(IVb)

wherein
- $R^a$ is an optically active and optionally substituted hydrocarbon group or an optically active and optionally substituted heterocyclic group,
- $R^5$ is an optionally substituted hydrocarbon group, an optionally substituted heterocyclic group, a group represented by the formula —$OR^6$ ($R^6$ is a hydrogen atom or an optionally substituted aliphatic hydrocarbon group) or a group represented by the formula —$NR^7R^8$ ($R^7$ and $R^8$ are the same or different and each is a hydrogen atom or an optionally substituted aliphatic hydrocarbon group),
- $Ar^1$ is an optionally substituted aromatic hydrocarbon group,
- ring A may be further substituted,
- n is an integer of 1–4, and
- * shows the position of an asymmetric carbon, or a salt thereof.

12. The compound of claim 11, wherein $R^aCO$— is a group represented by the formula

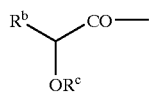
(IIIaa)

wherein $R^b$ is a $C_{6-14}$ aryl group and $R^c$ is a $C_{1-6}$ alkanoyl group or a $C_{1-4}$ alkyl group.

13. The compound of claim 11, wherein $R^aCO$— is a group represented by the formula

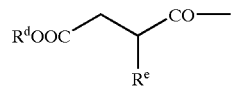
(IIIbb)

wherein $R^d$ and $R^e$ are the same or different and each is a $C_{1-4}$ alkyl group.

14. (6R)-6-({[(2S)-2-(Acetyloxy)-2-phenylethanoyl]-2-chloro-4-fluoroanilino}sulfonyl)-1-cyclohexene-1-carboxylic acid ethyl ester.

15. (6R)-6-({2-Chloro-4-fluoro[(2R)-4-methoxy-2-methyl-4-oxobutanoyl]anilino}sulfonyl)-1-cyclohexene-1-carboxylic acid ethyl ester.

16. (6S)-6-({[(2R)-2-(Acetyloxy)-2-phenylethanoyl]-2-chloro-4-fluoroanilino}sulfonyl)-1-cyclohexene-1-carboxylic acid ethyl ester.

17. (6S)-6-({2-Chloro-4-fluoro[(2S)-4-methoxy-2-methyl-4-oxobutanoyl]anilmo}sulfonyl)-1-cyclohexene-1-carboxylic acid ethyl ester.

18. The method of claim 2, wherein the group represented by the formula

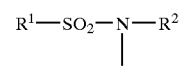

is a group represented by the formula

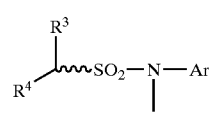
(A)

wherein $R^3$ and $R^4$ are the same or different and each is an optionally substituted hydrocarbon group or an optionally substituted heterocyclic group, $R^3$ and $R^4$ may form an optionally substituted cyclic group together with the adjacent carbon atom, Ar is an optionally substituted hydrocarbon group or an optionally substituted heterocyclic group, and the symbol ∿∿∿ indicates a racemate, and the diastereomer comprises a group represented by the formula

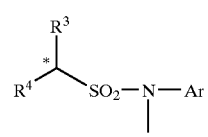
(A')

wherein * shows the position of the asymmetric carbon and other symbols are as defined above, which has a steric configuration of the asymmetric carbon of an R configuration or an S configuration.

19. The method of claim 3, wherein the group represented by the formula

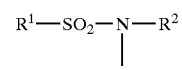

is a group represented by the formula

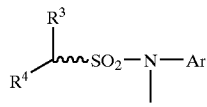
(A)

wherein $R^3$ and $R^4$ are the same or different and each is an optionally substituted hydrocarbon group or an optionally substituted heterocyclic group, $R^3$ and $R^4$ may form an optionally substituted cyclic group together with the adjacent carbon atom, Ar is an optionally substituted hydrocarbon group or an optionally substituted heterocyclic group, and the symbol ⁓
indicates a racemate, and the diastereomer comprises a group represented by the formula

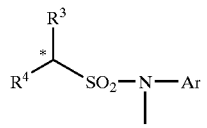
(A')

wherein * shows the position of the asymmetric carbon and other symbols are as defined above, which has a steric configuration of the asymmetric carbon of an R configuration or an S configuration.

20. The method of claim 4, wherein the group represented by the formula

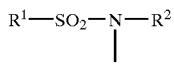

is a group represented by the formula

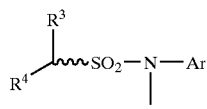
(A)

wherein $R^3$ and $R^4$ are the same or different and each is an optionally substituted hydrocarbon group or an optionally substituted heterocyclic group, $R^3$ and $R^4$ may form an optionally substituted cyclic group together with the adjacent carbon atom, Ar is an optionally substituted hydrocarbon group or an optionally substituted heterocyclic group, and the symbol ⁓
indicates a racemate, and the diastereomer comprises a group represented by the formula

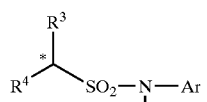
(A')

wherein * shows the position of the asymmetric carbon and other symbols are as defined above, which has a steric configuration of the asymmetric carbon of an R configuration or an S configuration.

21. The method of claim 5, wherein the group represented by the formula

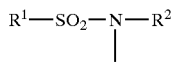

in the formulas (I) and (II) is a group represented by the formula

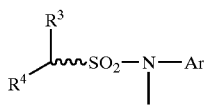
(A)

wherein $R^3$ and $R^4$ are the same or different and each is an optionally substituted hydrocarbon group or an optionally substituted heterocyclic group, $R^3$ and $R^4$ may form an optionally substituted cyclic group together with the adjacent carbon atom, Ar is an optionally substituted hydrocarbon group or an optionally substituted heterocyclic group, and the symbol ⁓
indicates a racemate, and the diastereomer comprises a group represented by the formula

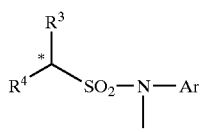
(A')

wherein * shows the position of the asymmetric carbon and other symbols are as defined above, which has a steric configuration of the asymmetric carbon of an R configuration or an S configuration.

22. The method of claim 2, wherein the group represented by the formula

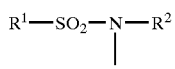

is a group represented by the formula

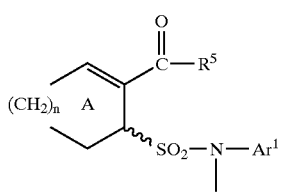
(B)

wherein $R^5$ is an optionally substituted hydrocarbon group, an optionally substituted heterocyclic group, the formula —$OR^6$ ($R^6$ is a hydrogen atom or an optionally substituted aliphatic hydrocarbon group) or the formula —$NR^7R^8$ ($R^7$ and $R^8$ are the same or different and each is a hydrogen atom or an optionally substituted aliphatic hydrocarbon group), $Ar^1$ is an optionally substituted aromatic hydrocarbon group, ring A may be further substituted, n is an integer of 1–4 and the symbol ⁓
indicates a racemate, and the diastereomer comprises a group represented by the formula is a group represented by the formula

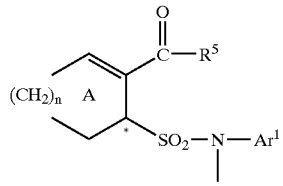
(B′)

wherein * shows the position of the asymmetric carbon and other symbols are as defined above, which has a steric configuration of the asymmetric carbon of an R configuration or an S configuration.

23. The method of claim 3, wherein the group represented by the formula

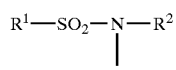

is a group represented by the formula

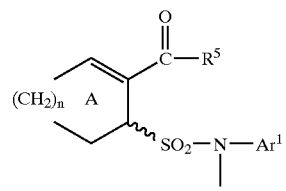
(B)

wherein $R^5$ is an optionally substituted hydrocarbon group, an optionally substituted heterocyclic group, the formula —$OR^6$ ($R^6$ is a hydrogen atom or an optionally substituted aliphatic hydrocarbon group) or the formula —$NR^7R^8$ ($R^7$ and $R^8$ are the same or different and each is a hydrogen atom or an optionally substituted aliphatic hydrocarbon group), $Ar^1$ is an optionally substituted aromatic hydrocarbon group, ring A may be further substituted, n is an integer of 1–4 and the symbol ∿∿∿
indicates a racemate, and the diastereomer comprises a group represented by the formula

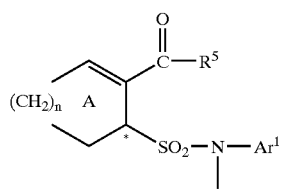
(B′)

wherein * shows the position of the asymmetric carbon and other symbols are as defined above, which has a steric configuration of the asymmetric carbon of an R configuration or an S configuration.

24. The method of claim 4, wherein the group represented by the formula

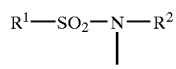

is a group represented by the formula

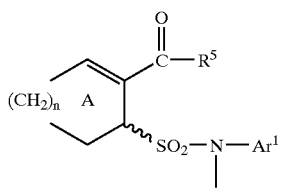
(B)

wherein $R^5$ is an optionally substituted hydrocarbon group, an optionally substituted heterocyclic group, the formula —$OR^6$ ($R^6$ is a hydrogen atom or an optionally substituted aliphatic hydrocarbon group) or the formula —$NR^7R^8$ ($R^7$ and $R^8$ are the same or different and each is a hydrogen atom or an optionally substituted aliphatic hydrocarbon group), $Ar^1$ is an optionally substituted aromatic hydrocarbon group, ring A may be further substituted, n is an integer of 1–4 and the symbol ∿∿∿
indicates a racemate, and the diastereomer comprises a group represented by the formula

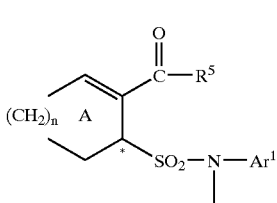
(B′)

wherein * shows the position of the asymmetric carbon and other symbols are as defined above, which has a steric configuration of the asymmetric carbon of an R configuration or an S configuration.

25. The method of claim 5, wherein the group represented by the formula

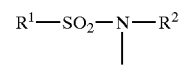

in the formulas (I) and (II) is a group represented by the formula

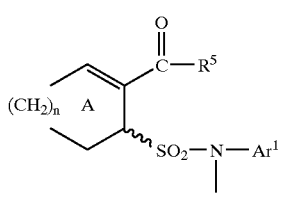
(B)

wherein $R^5$ is an optionally substituted hydrocarbon group, an optionally substituted heterocyclic group, the formula —$OR^6$ ($R^6$ is a hydrogen atom or an optionally substituted aliphatic hydrocarbon group) or the formula —$NR^7R^8$ ($R^7$ and $R^8$ are the same or different and each is a hydrogen atom or an optionally substituted aliphatic hydrocarbon group), $Ar^1$ is an optionally substituted aromatic hydrocarbon group, ring A may be further substituted, n is an integer of 1–4 and the symbol ∿∿∿
indicates a racemate, and the diastereomer comprises a group represented by the formula

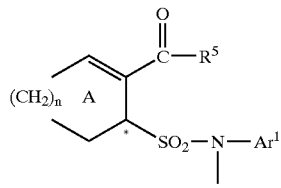
(B')

wherein * shows the position of the asymmetric carbon and other symbols are as defined above, which has a steric configuration of the asymmetric carbon of an R configuration or an S configuration.

26. The method of claim 2, wherein the group represented by the formula

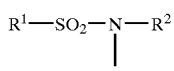

is a group represented by the formula

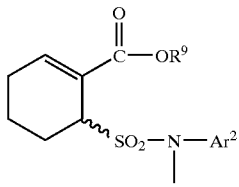
(C)

wherein $R^9$ is a $C_{1-6}$ alkyl group, $Ar^2$ is a $C_{6-14}$ aryl group optionally having a halogen atom, and the symbol $\sim\!\!\sim$ indicates a racemate, and the diastereomer comprises a group represented by the formula

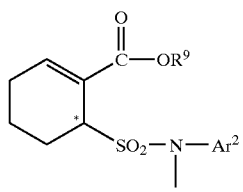
(C')

wherein * shows the position of the asymmetric carbon and other symbols are as defined above, which has a steric configuration of the asymmetric carbon of an R configuration or an S configuration.

27. The method of claim 3, wherein the group represented by the formula

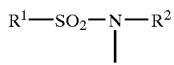

is a group represented by the formula

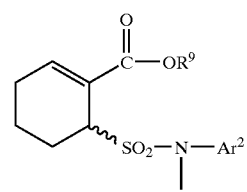
(C)

wherein $R^9$ is a $C_{1-6}$ alkyl group, $Ar^2$ is a $C_{6-14}$ aryl group optionally having a halogen atom, and the symbol $\sim\!\!\sim$ indicates a racemate, and the diastereomer comprises a group represented by the formula

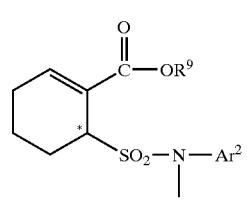
(C')

wherein * shows the position of the asymmetric carbon and other symbols are as defined above, which has a steric configuration of the asymmetric carbon of an R configuration or an S configuration.

28. The method of claim 4, wherein the group represented by the formula

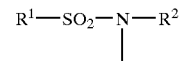

is a group represented by the formula

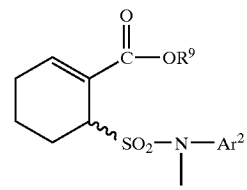
(C)

wherein $R^9$ is a $C_{1-6}$ alkyl group, $Ar^2$ is a $C_{6-14}$ aryl group optionally having a halogen atom, and the symbol $\sim\!\!\sim$ indicates a racemate, and the diastereomer comprises a group represented by the formula

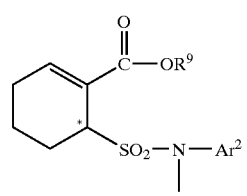
(C')

wherein * shows the position of die asymmetric carbon and other symbols are as defined above, which has a steric configuration of the asymmetric carbon of an R configuration or an S configuration.

29. The method of claim 5, wherein the group represented by the formula $R^1-SO_2-N-R^2$
       |
       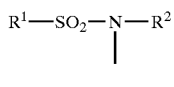

in the formulas (I) and (II) is a group represented by the formula

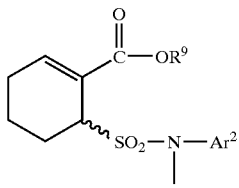
(C)

wherein $R^9$ is a $C_{1-6}$ alkyl group, $A^2$ is a $C_{6-14}$ aryl group optionally having a halogen atom, and the symbol  indicates a racemate, and the diastereomer comprises a group represented by the formula

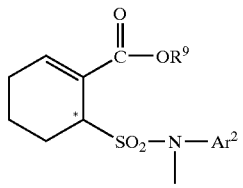
(C')

wherein * shows the position of the asymmetric carbon and other symbols are as defined above, which has a steric configuration of the asymmetric carbon of an R configuration or an S configuration.

30. The method of claim 5, wherein the group represented by the formula $R^a$—COOH   (III)

wherein $R^a$ is an optically active and optionally substituted hydrocarbon group or an optically active and optionally substituted heterocyclic group, is a compound containing an asymmetric carbon at the α-position of the carboxyl group.

\* \* \* \* \*